US005718915A

United States Patent [19]
Virtanen et al.

[11] Patent Number: 5,718,915
[45] Date of Patent: Feb. 17, 1998

[54] ANTIVIRAL LIPOSOME HAVING COUPLED TARGET-BINDING MOIETY AND HYDROLYTIC ENZYME

[75] Inventors: Jorma Virtanen; Sinikka Virtanen, both of Irvine, Calif.

[73] Assignee: Burstein Laboratories, Inc., San Juan Capistrano, Calif.

[21] Appl. No.: 424,874

[22] Filed: Apr. 19, 1995

Related U.S. Application Data

[63] Continuation-in-part of Ser. No. 332,514, Oct. 31, 1994.

[51] Int. Cl.$^6$ .......................... A61K 9/127; A61K 38/46; C12N 11/00; C12N 7/04

[52] U.S. Cl. .............. 424/450; 424/94.6; 424/94.61; 424/94.63; 435/174; 435/177; 435/236; 436/528; 514/44

[58] Field of Search .......................... 435/174, 175, 435/177, 180, 172.3, 236; 514/44; 935/54; 424/94.6, 179.1, 450, 94.61, 94.63; 436/528

[56] References Cited

U.S. PATENT DOCUMENTS

| | | | |
|---|---|---|---|
| 4,463,090 | 7/1984 | Harris | 435/7 |
| 4,722,906 | 2/1988 | Guire | 436/501 |
| 4,867,973 | 9/1989 | Goers et al. | 424/85.91 |
| 5,049,390 | 9/1991 | Wojdani | 424/450 |
| 5,168,057 | 12/1992 | Oh et al. | 435/174 |
| 5,273,743 | 12/1993 | Ahlem et al. | 424/85.8 |
| 5,279,833 | 1/1994 | Rose | 424/450 |
| 5,523,232 | 6/1996 | Sechler | 435/236 |
| 5,561,043 | 10/1996 | Cantor et al. | 435/6 |
| 5,591,448 | 1/1997 | Tepic | 424/450 |

OTHER PUBLICATIONS

Kuijpers et al., 1993, "Specific Recognition of Antibody—Oligonucleotide Conjugates by Radiolabeled Antisense Nucleotides: A Novel Approach for Two–Step Radioimmunotherapy of Cancer," *Bioconjugato Chem.* 4:94–102.

Nakagami et al., 1991, "Preparation of Enzyme–Conjugated DNA Probe and Application to the Universal Probe System," *Analytical Biochemistry* 198:75–79.

Watson et al., 1987, "Molecular Biology of The Gene," Fourth Edition, p. 266.

*Primary Examiner*—David M. Naff
*Attorney, Agent, or Firm*—Pennie & Edmonds LLP

[57] ABSTRACT

Complexes are prepared containing two or more different effector molecules joined to each other by a joining component. At least one of the effector molecules can bind to a target molecule and at least one of the other effector molecules has therapeutic properties. The joining component can be liposomes, proteins and organic polymers including dendrimer polymers, and can be of sufficient length and/or flexibility to permit the therapeutic effector molecule to interact with a target at the same time as the binding molecules. An antiviral liposome is prepared by coupling to a liposome outer surface a hydrolytic enzyme capable of digesting a viral component and a target-binding moiety which may be a polypeptide, glycoprotein or glycoprotein fragment having specificity for viruses such as HIV-1, influenza virus and hepatitis virus. The hydrolytic enzyme may be a glycosidase, phospholipase, lipase, cholesterol esterase, nuclease or protease. A second hydrolytic enzyme and target-binding moiety may also be present, and albumin may be coupled to the liposome surface. Within the liposome may be an internal hydrolytic enzyme capable of digesting a viral component.

28 Claims, 24 Drawing Sheets

SPACER (PEPTIDE)

TWO COMPLEMENTARY SINGLE STRANDED OLIGONUCLEOTIDES, WHICH FORM DOUBLE HELIX (3,3,3,3,3)

(1,1,7,8,8)

(8,9)    (9,8)

(3,4)    (4,7)

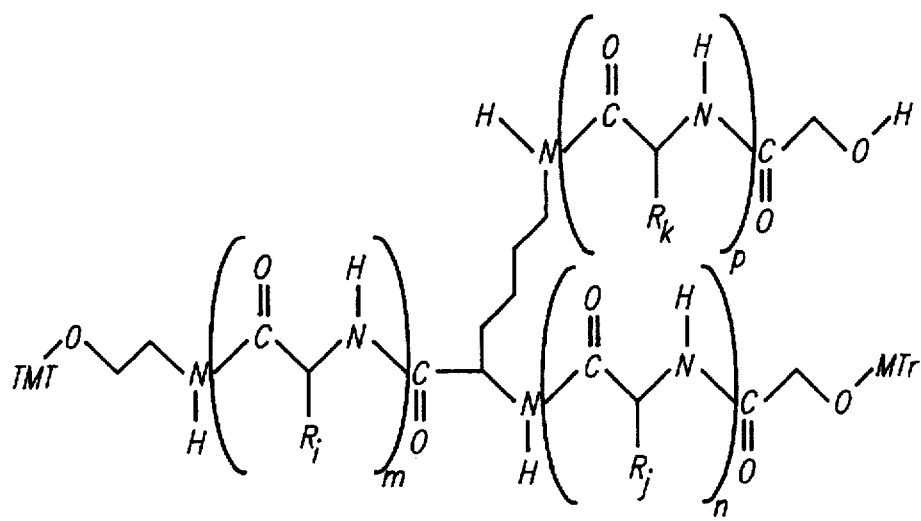
FIG. 11
FIG. 12
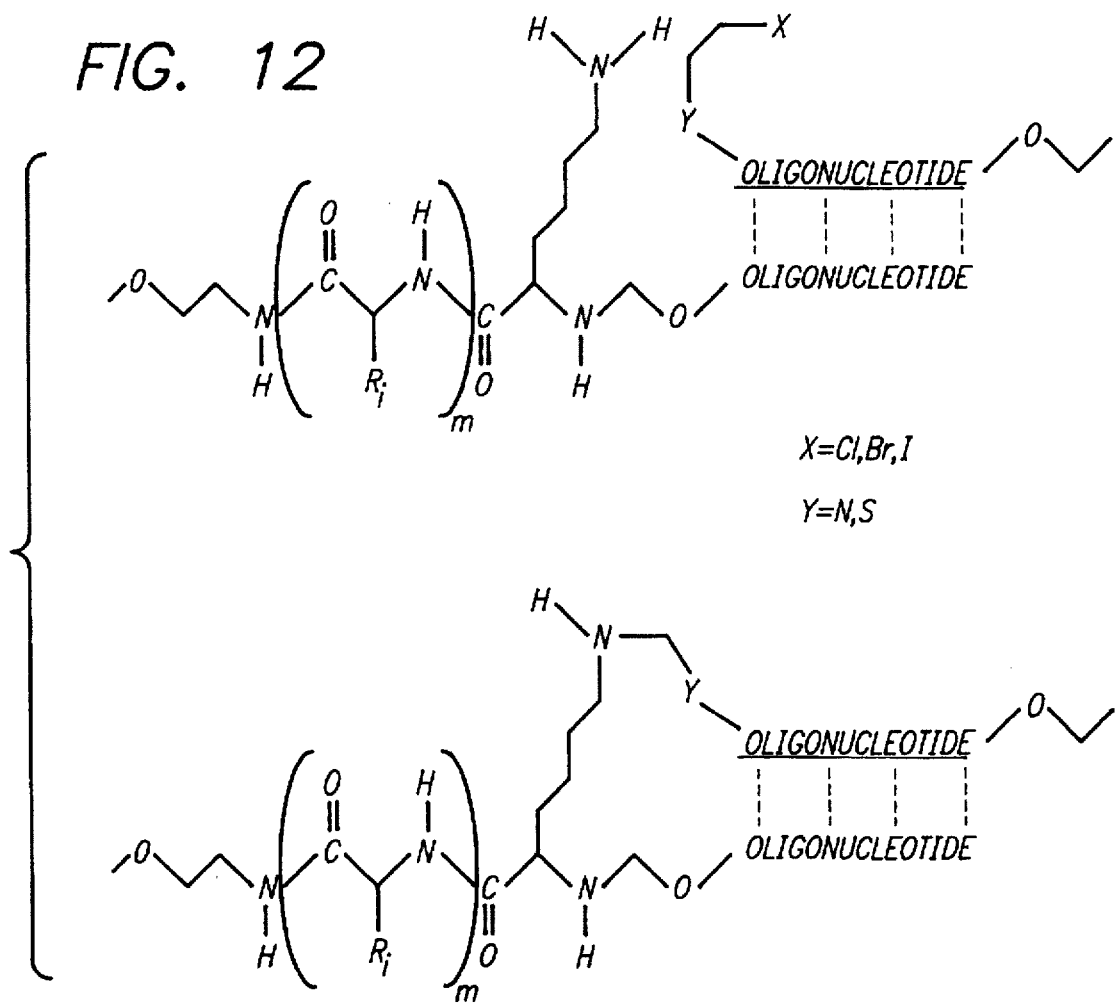
$X = Cl, Br, I$
$Y = N, S$

ANTIVIRAL LIPOSOME HAVING COUPLED TARGET-BINDING MOIETY AND HYDROLYTIC ENZYME

RELATED APPLICATIONS

This application is a continuation-in-part of copending U.S. application Ser. No. 08/332,514 filed Oct. 31, 1994, entitled "Complementarily Bonded Two And Three Dimensional Supramolecular Structures" hereby incorporated by reference.

FIELD OF THE INVENTION

The present invention is in the field supramolecular structures that specifically bind to a selected target.

BACKGROUND

Organized molecular systems are well known in biology and chemistry. For example, pure molecular compounds form crystals, and surface active molecular compounds form monolayers at air-water interphase and vesicles in water. Bilayers of liposomes mimic biological membranes, and biological membranes are good examples of multimolecular organized systems. Viruses, in particular, are highly organized supramolecular assemblies whose complexity surpasses any man-made assembly. Another prime example is the DNA double helix, which is the result of highly selective interaction of two complementary single strand molecules. Man made, or artificial examples of supramolecular systems, include cryptates, i.e., inclusion complexes of macrocyclic receptor molecules, and interrupting two dimensional hydrogen bonded network by a large capping molecule. In these state-of-the-art examples, the structure of all participating molecules are highly specific.

Jean-Marie Lehn has defined supramolecular chemistry as the chemistry beyond individual molecules, i.e., the chemistry of the intermolecular bond. Early work in supramolecular chemistry involved crown ethers and cryptates, compounds based on the interaction of electron pair and ion and possibly additional ion-ion interaction (J.-M. Lehn, Angew. Chem. Int. Ed. Engl. 29 (1990) 1304–1319).

Oligobipyridines form in the presence of suitable metal cations such as copper(II) double-stranded helicates. Auxiliary groups may be attached into bipyridine units. If these groups are nucleotides they may serve as recognition sites for DNA (U. Koert, M. M. Harding and J.-M. Lehn, Nature (1990) 346:339).

Most previously described hydrogen bonded supramolecules are supramolecular polymers, i.e., periodic supramolecules composed of one or two repeating units. In principle the number of repeating units of polymeric supramolecules may be larger than two but until now nobody has used more than two repeating units. Examples of this class of supramolecules includes the chain-like supramolecule formed by co-crystallization of 1:1 mixture of 2,4,6-triaminopyrimidine and a suitable barbituric acid derivative (J.-M. Lehn, M. Mascal, A. DeCian, J. Fisher, J. Chem. Soc. Chem. Commun. (1990) 479).

Polymeric supramolecules formed from a single unit may also be used. For example, a tubular supramolecule has been formed from a single cyclic peptide (M. R. Ghadiri, J. R. Granja, R. A. Milligan, D. E. McRee and N. Khazanovich, Nature (1993) 366:324–327). These polymeric supramolecules are often simply crystals or mixed crystals in which hydrogen bonding plays a predominant role in structure maintenance. Even, if these supramolecules are stable in solution, their size is variable like that of a conventional polymer.

A step towards controlling supramolecular size and shape has been the use of capping molecules to interrupt the molecular association at the desired point (J. P. Mathias, C. T. Seto, J. A. Zerkowski and G. M. Whitesides in "Molecular Recognition: Chemical and Biochemical Problems II" (Ed. S. M. Roberts) Royal Society of Chemistry). A mixture of he isocyanurate derivative ($benzCA_2$) and trismelamine derivative ($trisM_3$) gives the supramolecule $(trisM_3)_2 (benzCA_2)_3$. This strategy typically produces supramolecules which have 'molecular weight' of 4–10 KDa.

No process exists today for creating large molecular assemblies of deliberately chosen molecules in which the location of the molecules in the assembly can be selected accurately with respect to each other. Nonetheless, a dire need exists for such molecular structures since they could have numerous important medical, chemical and physical applications. These applications include, but are not limited to, supramolecular drugs, drug delivery to target organs, capture of viruses and catalysts, sensors and nanotechnological components.

Polypeptides and proteins, especially enzymes, have been attached to oligonucleotides. A peptide or protein has been used as a tag for an oligonucleotide or oligonucleotide is used as a tag for a polypeptide. Techniques such as ELISA allowed to trace enzymes easier than oligonucleotides, enzymes were used as tags for oligonucleotides. PCR provides for assays of extreme sensitivity. Oligonucleotides are often used as a tag for polypeptides or peptidomimetics, so that the fate of the polypeptide can be followed in vitro or in vivo. Synthesis methods which are used to prepare these conjugates are also useful in this invention. (D. Pollard-Knight, Technique (1990) 3:113–132).

Linear single-stranded tRNA forms branched structures because there are several complementary pieces of the sequence are suitably located. Recently, several two and three dimensional structures have been formed using this principle (Y. Zhang and N. C. Seeman, J. Am. Chem. (1994) 116:1661–1669; N. C. Seeman, J. Theor. Biol. (1982) 99:237–247.). These DNA based supramolecules have been bound together to form active structures. Because several steps are typically needed to create these molecules, the overall synthesis yield can be very low (0.1–1%) because of these steps alone.

Branched pre-mRNA is found in cells. These molecules have highly specific structures in which adenosine is always linked to guanosine. These branched RNAs have been synthesized (T. Horn and M. S. Urdea Nucleic Acid. Res. (1989) 17:6959–6967; C. Sund, A. Földesi, S.-I. Yamakage and J. Chattopahyaya, Nucleic Acid. Res. (1991) 9–12). The synthesis of branched nucleic acids has been extended to the synthesis of nucleic acid dendrimers (R. H. E. Hudson and M. J. Damha, J. Am. Chem. Soc. (1993) 113:2119–2124).

Oligonucleotide comb and fork structures have been used for analytical purposes (M. S. Urdea, B. Warner, J. A. Running, J. A. Kolberg, J. M. Clyne, R. Sanchez-Pescador and T. Horn (Chiron Corp.) PCT Int. Appl. No. WO 89/03, 891 05 May 1989, U.S. Appl. No. 109,282, 15 ohm Oct. 1987. 112 pp).

All previously known supramolecular structures have some drawbacks. It is of interest to provide novel supramolecular structures that may be adapted for a variety of uses, including disease therapy, diagnostics, assays, and electronics.

SUMMARY OF THE INVENTION

The present invention provides several different binding molecule-multienzyme complexes capable of specifically binding to a target of interest. The binding molecule-multienzyme complexes of the invention comprise two or more different effector molecules joined to each other by a joining component, wherein at least one of the effector molecules has the property of binding to a molecular target, i.e. a binding effector molecule, and at least one of the other effector molecules is a therapeutic effector molecule. The joining components for use in the binding molecule-multienzyme complexes of the invention may be of a variety of classes including liposomes, proteins, organic polymers (including dendrimer type polymers). Another aspect of the invention to provide binding molecule-multienzyme complexes in which the joining component is of sufficient length and/or flexibility to permit the therapeutic effector molecules to physically interact with the same target as binding molecule at the same time as binding effector molecule is interacting with the target.

One aspect of the invention relates to binding molecule-multienzyme complexes that are supramolecules formed by at least two supramolecular component molecules. Each supramolecular component molecule comprises at least one effector molecule and at least one nucleic acid chain. At least one of the nucleic acid chains on at least one component molecule of the supramolecules of the invention are complementary to nucleic acid chains on at least one other component, and thus are able to bind the components of the supramolecule by the formation of double stranded nucleic acid chains between the complementary chains. The present invention also provides methods of making the supramolecules of the present invention.

The nucleic acid chains of the supramolecules of the invention are preferably DNA, RNA and may also contain structural analogues of DNA or RNA. Effector molecules that may be used to form the supramolecules include, but are not limited to polypeptides, proteins, lipids, sugars. These effector molecules may impart chemical and physical properties to the supramolecule include, hydrophobicity, hydrophilicity, electron conductivity, fluorescence, radioactivity, biological activity, cellular toxicity, catalytic activity, molecular and cellular recognition and in vivo transport selectivity.

Another aspect of the invention is to provide binding molecule-multienzyme complexes of the invention that may be used to treat or prevent infectious diseases, particularly viral infectious diseases. Binding molecule-multienzyme complexes suitable for the treatment and/or prevention of infectious diseases comprise effector molecules that are antibodies specific for one or more antigen on a viral particle and one or more enzyme capable of catalyzing a reaction that destroys the infectivity of the virus of interest, e.g., hydrolysis of viral coat proteins or viral envelope lipids.

An effector molecule for use in the invention may also be a toxin, such as ricin, which will kill the cell, if the virus is internalized. Another aspect of the invention is to provide binding molecule-multienzyme complexes adapted for the treatment of non-infectious diseases. Binding molecule-multienzyme complexes for the treatment of specific diseases may comprise binding effector molecules specific for certain cells or tissues and effector molecules that serves to directly alleviate a given disease condition.

Another aspect of the invention is to provide binding molecule-multienzyme complexes that expedite the delivery of polynucleotides and other macromolecules into the interior of cells. Such binding molecule-multienzyme complexes are supramolecular structures derived from two or more supramolecular components adapted for the internalization of macromolecules may comprise effector molecules that either alone, or in combination with other effector molecules, on the same or different structure, that are capable of crosslinking receptors on the surface of a cell for transformation.

Another aspect of the invention is to provide binding molecule-multienzyme complexes useful for performing assays for compounds of interest, particularly immunoassays. Supermolecular structures for use in assays typically comprise an effector molecule capable of specifically binding to a compound of interest and a second effector molecule that may capable of producing a detectable signal, e.g., an enzyme, or a second molecule capable of specifically binding to a compound of interest. Another aspect of the invention is to provide assays employing binding molecule-multienzyme complexes of the invention so as provide for the detection and/or quantitation of compounds of interest.

Another aspect of the invention is to provide binding molecule-multienzyme complexes useful for the prevention and treatment of atherosclerosis and related cardiovascular disorders. Binding molecule-multienzyme complexes of the invention useful for the treatment of such diseases may comprise an effector molecule that is an antibody specific for antigens in atherosclerotic plaque.

BRIEF DESCRIPTION OF THE FIGURES

The invention will be better understood by reference to the appended Figures, of which:

FIG. 5 is a schematic representation of the construction of a supramolecule for surrounding an icosahedral virus.

FIG. 11 illustrates an example of a second spacer molecule for connecting three nucleotides to an effector molecule.

FIG. 12 illustrates an example of a method for cross-linking two complementary oligonucleotides at one end.

DETAILED DESCRIPTION OF THE INVENTION

The present invention relates to composition of matter that have the property of specifically binding to selected molecular targets of interest, and directing a therapeutic agent to the binding site. The compounds of the invention are collectively referred to as of the invention comprise two or more different effector molecules joined to each other by a joining component, wherein at least one of the effector molecules is a binding effector molecule and at least one of the effectors is a therapeutic effector. The joining component may be any of a variety of forms including liposome, proteins, organic polymers, and the like.

One of the types of binding molecule-multienzyme complexes of the invention are supramolecules (also referred to herein as supramolecular assemblies and supramolecular constructions) that comprise at least two components, i.e., supramolecular components. Each supramolecular component comprises an effector molecule and at least one nucleic acid chain covalently joined to the effector molecule. By placing complementary nucleic acid chains on different components, the components of the supramolecule may be bound together by the associative forces, i.e., hydrogen bonding, between the complementary nucleic acid chains, thereby producing supramolecular constructions in which two or more effector molecules are joined to one another a double-stranded or partially double stranded nucleic acids.

Figure 1:
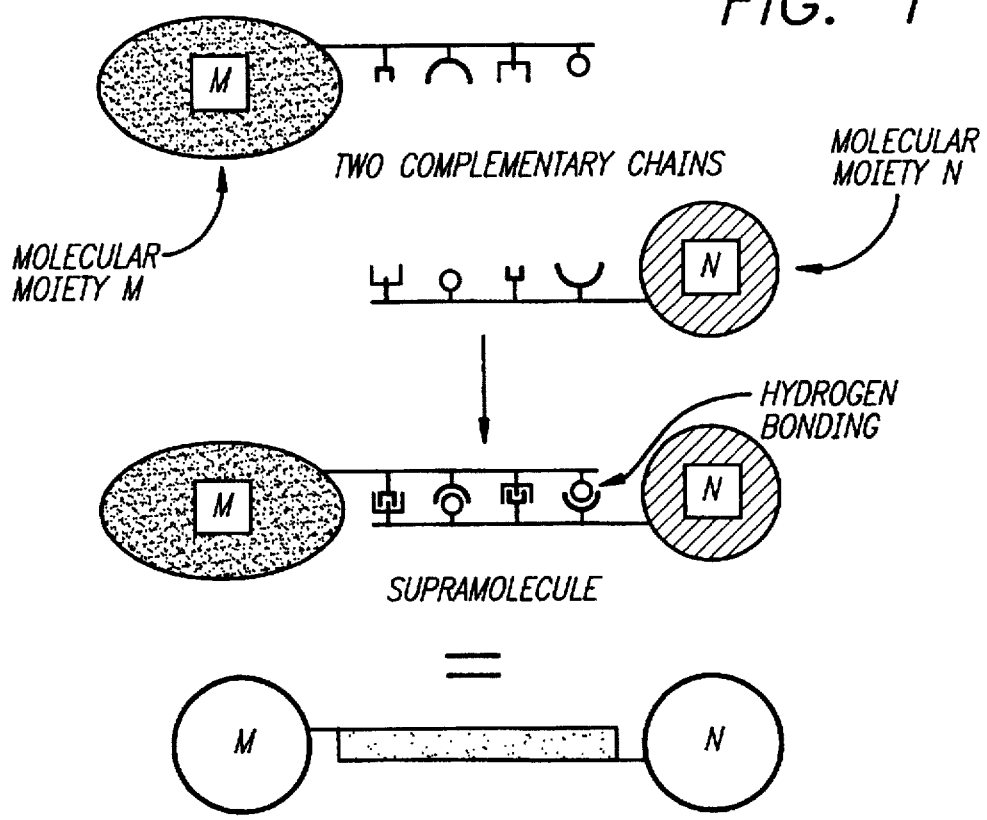
FIG. 1 is a schematic representation of the construction of a supramolecule constructed from two components.

The general concept of the supramolecular assembly embodiment of the invention may be better understood by reference to FIG. 1 wherein supramolecular components A and B ar joined by effector molecules M and N, respectively. Components A and B are bound to each other by the double stranded nucleic acid chain formed by complementary nucleic acid chains.

There is no theoretical limit to the number of supramolecular components that may be used to construct a particular supramolecular assembly. Rather, steric factors that could limit the number of components that can be used in a particular supramolecule may be avoided by proper design of the supramolecule using basic structural information that is well known to the person of ordinary skill in the art of biochemistry. Thus the invention provides for numerous compounds that are supramolecular assemblies, i.e., supramolecules, comprising two or more supramolecular components of the invention. The supramolecular components of the invention comprise an effector molecule, e.g., an antibody, covalently joined to at least one polynucleotide. Two or more supramolecular components of the invention may be joined to one another by means of the nucleic acids moieties of the supramolecular components by employing nucleic acids that have regions of complementarily or partial complementarily to one another. Thus two or more effector molecules may be joined to one another by double stranded or partially double stranded nucleic acids.

Any class of molecule can be used as effector molecule component of the subject binding molecule-multienzyme complexes. Suitable molecules for use as the effector molecule moieties of the subject binding molecule-multienzyme complexes include, but are not limited to, sugars, peptides, lipids, polymers. The effector molecules of the binding molecule-multienzyme complexes may serve several different functions within the binding molecule-multienzyme complexes. For example, the effector molecules may be used to provide a wide array of structural features to binding molecule-multienzyme complexes. In addition, the effector molecules can also provide certain chemical and physical properties to the binding molecule-multienzyme complexes, which include, but are not limited to, hydrophobicity, hydrophilicity, electron conductivity, fluorescence, radioactivity, biological activity, cellular toxicity, catalytic activity, as well as molecular and cellular recognition and in vivo transport selectivity. Effector molecules include a variety of protein type, including toxins, proteinases, receptors, ligands, lectins, antibodies, esterases, hormones, cell surface markers, etc.

Some effector molecules are referred to herein as "binding effector" molecules. Binding effector molecules have the property of specifically binding to one or more molecules of interest, i.e., target molecules. A given binding effector molecule has the property of being a binding effector molecule with respect to target molecules. Effector binding molecules may be either a member of a pair of specific binding molecules, e.g., an antibody-hapten pair or a receptor-ligand pair. Examples of binding effector molecules include, but are not limited to, antibodies, integrins, adhesins, cell surface markers, T cell receptors, MHC proteins, and the like.

Another class of effector molecules are referred to herein as "therapeutic effector molecules". Therapeutic effector molecules are either (1) biologically active molecules, including but limited to, enzymes, drugs, prodrugs, enzymes, ligands specific for receptors, radionuclides, and toxins or (2) detectable labels, including, but not limited to fluorophores, enzymes, and radionuclides. A given therapeutic effector molecule may be both a biologically active molecule and detectable label. The following are some examples of therapeutic effector molecules that have been used to treat various diseases. These therapeutic effector molecules may readily be adapted for use in the claimed invention. Thrombolytic therapy is well established in the treatment of acute myocardial infarction (Z. Bode, et. al., Z. Kardiol 83 (1994) 393). Proteinases which have been approved for this purpose include urokinase and streptokinase. Recombinant plasminogen activator, which activates plasminogen occurring naturally in the blood, is also in common use. Proteolytic enzymes have been also used to treat disk herniation (chymopapain, L. G. Lenke, et. al., AORN J. 59 (1994) 1230), fallopian tube (chymotrypsin, chinese) and inflammation (carboxypeptidase N, M. Rybak et. al. Pharmacology 16 (1978) 11). Other enzyme therapies studied include: Adenosine deaminase, DNAse (cystic fibrosis), Glucosylceramidase (Gaucher's disease), Lipase (cystic fibrosis, G. Morrison et. al., Aliment Pharmacol. Ther. 6 (1992) 549; cancer B.A. Richards, J. R. Soc. Med. 81 (1988) 284), Lysozyme (immunostimulant; antibacterial agent, I.A. Vereshchagin and O.D. Zhuravleva, Vrach. Delo (1994) 103), Peptide hydrolases (antiviral agents, K. N. Veremeenko, Vrach. Delo (1994) 8), Superoxide dismutase, Terrilytin (immunostimulant), Ribonuclease (antibacterial, antiviral, antitumor), Phospholipase A2 (autoimmune suppression, K. Mahlberg, et. al., Acta Ophthalmol. Suppl. 182 (1987) 166); arthritis, R. B. Zurier, et. al., Ann. Rheum. Dis. 32 (1973) 466), Phospholipase C (pulmonary microembolism, I.G. Jansson, et. al., J. Trauma 28 (1988) S 222.

The binding molecule multienzyme complexes of the invention comprise at least one binding effector molecule and at least one therapeutic effector molecule. The binding molecule-multienzyme complexes may comprise more than one different type of binding effector molecule and may contain more than one molecule of each type of binding effector molecule. Similarly, the binding molecule-multienzyme complexes of the invention may comprise more than one different type of therapeutic effector molecule and may contain more than one molecule of each type of therapeutic effector molecule present in the effector molecule. The specific effector molecules within a given binding molecule-multienzyme complexes may be selected so that the target component molecule has therapeutic value for a given disease or diseases. The person of ordinary skill in the art, given the information provided herein, will readily be able to select appropriate effector molecules to treat a disease of interest. For example, a target multi-component therapeutic molecule for the treatment of a viral disease may comprise an antibody specific for a viral coat protein or viral envelope lipid as a binding effector molecule and a proteinase specific for the same viral coat protein as a therapeutic effector molecule.

The nucleic acid used to join the subject supramolecular components to each other in some embodiments of the invention, i.e., targeted multi-component supramolecules comprising two or more supramolecular components, are preferably between 5 and 100 bases in length, although nucleic acids may be significantly longer than 100 bases. The nucleic acid portion of the subject supramolecular components and supramolecular assemblies may be any of the wide variety nucleic acid molecules, either naturally occurring, e.g., RNA or DNA, or synthetic analogs, e.g., phosphorothioates. The term "nucleic acids" as used herein, unless indicated otherwise, refers to both naturally occurring nucleic acids and synthetic analogs thereof. For many applications, it may be desirable to use synthetic analogs of natural nucleic acid rather than nucleic acids because of certain properties specific to the analogs e.g., nuclease resistance and higher denaturation temperatures of double-stranded nucleic acids.

Detailed descriptions on the use and synthesis of nucleic acid analogs can be found, among other places, in U.S. Pat. No. 5,292,875 (phosphorothioates), U.S. Pat. No. 5,218,103 (thiophosphoramidites), U.S. Pat. No. 5,183,885 (phosphorothioates), U.S. Pat. No. 5,151,510 (phosphorothioates), U.S. Pat. No. 4,814,448 (phosphonates), U.S. Pat. No. 4,096,210 (phosphorates) U.S. Pat. No. 4,094,873 (phenylphosphorothioates), Ragle et al., Nuc. Acids. Res. 18(6):4751–4757 (1990) (phosphoramidates). Information on how to synthesize conventional nucleic acid can be found, among other places, in Eckstein Oligonucleotide and Analogues: A Practical Approach Oxford University Press (1992). The complementary nucleic acids need not necessarily be entirely complementary with respect to one another. A nucleic acid of a first supramolecular component may be complementary to only a portion of the nucleic acid moiety of a second supramolecular component or the complementarity may be over the entire length of the nucleic acid. Nucleic acid moieties of the subject supramolecular components may contain multiple regions of complementarily to two or more nucleic acids moieties on additional supramolecular components thereby to be joined to permitting three or more supramolecular components to be joined to one another through hybridization. The complementarily (as measured by sequence homology) may be either 100 percent or less. It will be appreciated by those of ordinary skill in the art that the strength of associating, as indicated by duplex nucleic acid melting point, may be modulated by controlling factors such as the degree of complementarily, the identity of the base pairs (e.g., GC rich nucleic acids have a higher Tm than AT rich nucleic acids), the choice of a nucleic acid or nucleic acid analog, the length of the region of complementarily, and the like. The nucleic acid moieties of the subject supramolecular components may be linear or branched. Methods of producing branched nucleic acids are known to the person skilled in the art, and example of how to make branched nucleic acid molecules can be found in PCT Publication No. WO 89/03891. The use of branched nucleic acids as the nucleic acids as the nucleic acid moieties of the subject supramolecular components is particular interest because branched nucleic acid may be used to conveniently join three or more supramolecules components to one another through hybridization of the nucleic moieties. Triple and tetra helixes of nucleic acid chains can also be used in the supramolecules in order to provide other structural characteristics, such as rigidity, to the supramolecule.

Figure 2A:
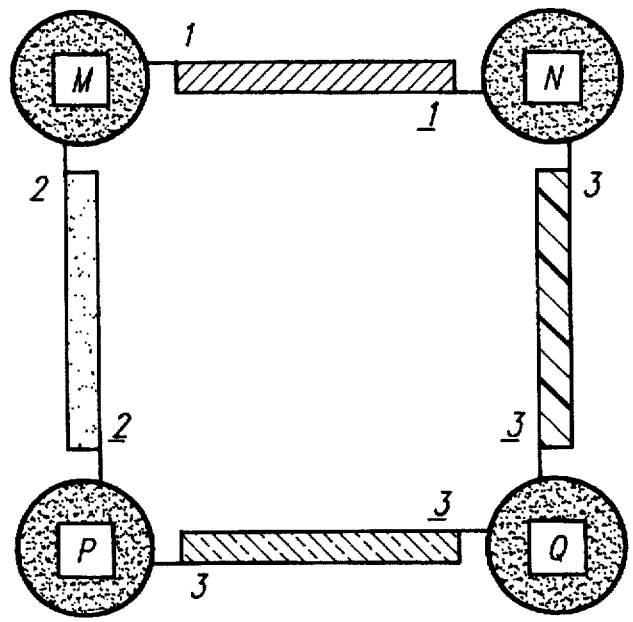
FIG. 2(A) is a schematic representation of the construction of a square planar supramolecule constructed from four components.

The length of the nucleic acid moieties as well as the position of the complementary base on the nucleic acids may be used to control the two and three dimensional shape of the supramolecule. For example, as depicted in FIG. 2(A), a square supramolecule can be prepared by employing four components which each contain two nucleic acid chains of equal length. Similarly, as also depicted in FIG. 2(C), a tetrahedral supramolecule can be formed using four components. As can be seen from FIGS. 2(A) and 2(C), a wide variety of two and three dimensional supramolecule structures may be formed using differing numbers of components and differing numbers of complementary nucleic acid chains. For example, supramolecules of the present invention may contain geometric configurations that generally resemble triangles, squares, pentagons, hexagons, heptagons, octagons, parallelograms, pyramids, tetrahedrons, cubes and cylinders. It should also be understood that these figures are merely schematic representations of supramolecular assemblies and that the supramolecule may not actually possess these geometric structures in solution or in crystalline form because of the due to the flexibility of double stranded nucleic acid chains as well as other solvation, electronic and stearic factors that may be present in a given supramolecule.

With respect to each supramolecular component, the number of nucleic acid moieties that may be attached to a particular effector molecule may be varied greatly so as to produce supramolecular assemblies of the desired structure. Supramolecular components of the invention may comprise one or more nucleic acid moieties. The total number of nucleic acid moieties that may be attached to an effector molecule is limited by stearic hinderance and the number of potential attachment sites, problems which may be avoided by proper selection of the effector molecule and the nucleic acid moieties.

In another embodiment of the supramolecular components of the invention, more than one effector molecules may be joined to a single nucleic acid molecule. Such supramolecular components comprising a plurality of effector molecules joined to a single nucleic acid molecule may be used to form supramolecular assemblies through a nucleic acid hybridization with the nucleic acid moieties of similar supramolecular components or supramolecular components in which nucleic acid moieties are joined to only a single effector molecule.

In a preferred embodiment of the binding molecule-multienzyme complexes of the invention the individual effector molecules are joined to one another by a joining component (or joining means) that gives the individual effector molecules within the binding molecule-multienzyme complexes operational freedom, i.e., freedom of movement sufficient to permit a therapeutic effector component to physically interact with the same target as a binding effector component of the same binding molecule-multienzyme complexes when the binding effector component is bound to the target. Several different types of molecules and multi-molecular assemblies may serve as joining components in different embodiments of the invention. The embodiment of the invention in which the various effector molecules are interconnected by joining components that permit the effector molecules to have the aforementioned degree of operational freedom are not limited by the examples provided herein. The person of ordinary skill in the art of chemistry and/or molecular biology will be able to devise numerous joining components having the desired characteristics. For example conventional bifunctional linker molecules may be modified a person of ordinary skill in the art organic chemistry go as have sufficient length to function in the joining of effector molecules with operational freedom. In one embodiment of the invention, the joining component is a liposome, i.e. the binding molecule-multienzyme complexes is a liposome comprising a target binding molecule and a therapeutic effector molecule. In another embodiment of the invention, the joining component is a peptide, i.e. binding molecule-multienzyme complexes is a peptide, i.e. binding molecule-multienzyme complexes comprises a binding effector molecule and a therapeutic effector molecule joined to each other through a peptide. In another embodiment of the invention, the joining component is a dendrimer, i.e., binding molecule-multiemzyme complexes is a dendrimer comprising a binding effector molecule and a therapeutic effector molecule.

When the binding molecule-multienzyme complexes of the invention comprises a liposome. The effector molecules are covalently attached to one or more constituent lipids of the liposome. The effector molecule may be directly coupled to the lipid, or coupled through a linker. Linkers serving to couple an effector molecule to a lipid may be of a variety of compounds, including polynucleotides. The liposome may optionally comprise one or more therapeutic effector molecules in the internal compartment of the liposome as well as covalently attached to the surface of the liposome. Liposomes can be classified as small unilamellar vesicles, large unilamellar vesicles, cell-size unilamellar vesicles and multilamellar vesicles (J. M. Wrigglesworth in Membrane Processes, Molecular Biology and Medical Applications (Eds. G. Benga, H. Baum and F. A. Kummerow), Springer-Verlag, New York, 1984). Methods of preparation of these liposomes include vortexing, sonication, detergent dialysis or dilution, infusion or reverse phase evaporation, fusion methods, addition of short-chain PC's, addition of fatty acids or detergents, rapid extrusion and transient increase in pH.

The simplest way to prepare liposomes is to add water onto the dry components, and mix. The power used in the mixing determines the size of the liposomes. Other possibility is to use small molecular weight detergents to solubilize the lipid-protein components and phospholipids. The detergent is dialyzed off the solution and liposomes form spontaneously. Also the pure lipid liposomes can be prepared in a controlled manner and lipid-protein conjugates may be added later in a detergent solution. Lipid part of the conjugate will penetrate into the bilayer and the proteins will be anchored. The detergent can be dialyzed away. This approach uses relatively small amount of detergent, which can be biocompatible, and need not be removed.

The lipid part of a liposome that is coupled to an effector molecule that is a protein preferably contains primary amino or thiol group in their polar head group. Accordingly, phosphatidylethanolamines can be directly used. Thiol groups can be introduced into synthetic phospholipids, although it is not a part of natural lipids. In order to anchor the lipid-protein conjugate firmly into the liposome the lipophilicity of the lipid should be increased. This can be achieved in several ways. First, the length of the alkyl chains in the lipid can be significantly increased (about $C_{30}$) compared what is normally used (about $C_{18}$) in liposomes. Secondly, the number of alkyl chains in one lipid molecule can be higher than two, e.g., five alkyl chain phospholipid can be conveniently prepared starting from mannitol. Alternatively, several phospholipid molecules can be chemically coupled through their polar head groups into a controlled multimer, which is further conjugated with a protein. Thirdly, phospholipids that are thermophilic bacterial phospholipids, or an analog thereof can be used. These phospholipids are formally like phospholipid dimers, in which the two phospholipids are connected via their alkyl tails. Either one or both alkyl tails can be connected. Thus, a monomolecular layer in a liposome may look like a bilayer formed by a normal phospholipid. The stability of the liposomes formed by these 'dimeric' phospholipids is very high. Fourthly, polymerizable phospholipids can be used. The polymer is preferably biocompatible and biodegradable, preferably a polyester or a polyamide.

The lipid component of the embodiments of the subject binding molecule-multienzyme complexes that are liposomes are preferably not substrates of lipolytic enzymes used as effector molecules. When lipase and phospholipase $A_2$ are used as an effector molecule, the lipids must be resistant against these enzymes. If ether bonds are used to connect alkyl chains with glycerol or other polyalcohols, the resistance is automatically attained, because these two enzymes are ester hydrolases. Enzymes are also sensitive for the stereochemistry of the lipid. Use of unnatural stereochemistry reduces or completely inhibits enzymatic activity. The liposomal lipid bilayer can be highly analogous to lipid part of cellular membranes. The liposomes of this invention may also comprise proteins in addition to the effector molecules. These proteins are not normal membrane proteins and their concentration in the blood is very low. In order to make these liposomes to resemble normal blood component or cell, additional proteins may be attached onto their surfaces. Possible proteins include albumin and glycophorin. Albumin is a molecular level scavenger, which removes fatty acids and lysolipids. These lipids are formed via the action of the lipolytic enzymes, which are a part of the liposome. Thus, albumin is an ideal additional component of the liposome, because it can perform a double function: camouflage and scavenging the hydrolytic products. Glycophorin is a membrane bound glycoprotein. It will make these liposomes to look like cells to some degree.

An advantage of the liposomes is that the number of effector molecules can be easily adjusted without affecting the size of the liposome. The various components may be supposed to be randomly distributed over the surface. Because of the rapid diffusion, the effector molecules which are needed to perform a certain function, are available when needed. Once binding effector molecules makes a contact with the target, other adhesion molecules will diffuse to the vicinity of the contact site and will bind to the target. Most targets have several binding sites near each other. The strong binding between binding effector molecules and their targets is preferred, but is not necessary for the liposomes containing digestive enzymes. For instance, by removing the lipid coat of the HIV-1, the protein core of the virus will dissolve and RNA is exposed. This happens when the virus is internalized by the cell. The lipid bilayer of the virus will fuse with the cellular membrane and the RNA is released. This is in contrast to influenza virus, which has an endocytosis pathway. The infected cell dismantles the influenza virus in lysosomes using lipases and proteases. For HIV-1 proteases are not needed. Thus, proteases are not required needed to inactivate HIV-1 and similar viruses, while for influenza virus and other viruses with a similar life cycle, proteases may be effective for inactivating the virus. The liposome internal compartment may also comprise an antisense oligonucleotide or other therapeutic compound such as a drug or enzyme. In some embodiments of the invention, the liposomes may comprise a DNAse or RNAse in the internal compartment of the liposome or as therapeutic effector molecules on the surface of the liposome.

Many naturally occurring proteins may be used without any modification as effector molecules. Because in some cases these liposomes are used in vivo in humans, the human proteins should be used to avoid unwanted immune responses. Human proteins can be produced in transgenic plants or animals. The amino acid sequence of proteins may also be altered through well-known genetic engineering techniques to produce mutated proteins having the desired biological functions of corresponding naturally occurring protein, but adapted to coupling to lipid molecules. For example, addition of a cysteine residue, either through substitution or inserting, will add a free thiol group for coupling to a lipid molecule. Moreover the location of this cysteine can be deliberately chosen. It should be located so that conjugation does not disturb the activity of the protein. Normally this means that the cysteine must be as far as possible from the active site.

In order to covalently couple a lipid with an effector molecule, the lipid must contain a functional group which has high enough reactivity with heterobifunctional crosslinker. Phosphatidylethanol-amines (PE) have free aliphatic amino group and can be used directly for conjugation. The conjugation of phosphatidylethanolamines (PE) and serines (PS) with proteins is well known in the literature (Egger et. al. Biochem. Biophys. Acta 1104 (1992) 45–54). Especially, if the protein contains a thiol group, a chemically well defined conjugate can be easily prepared. Several spacers are commercially available to couple two molecules, which contain an amino and a thiol group. If a protein does not contain an a thiol group, an aliphatic amino group, may be used for conjugation. Thiol groups are preferred for conjugation sites in proteins as compared with amino groups because of the lower abundance of thiol groups in most proteins.

Proteins can also be conjugated with lipids after the preparation of the liposomes so as to position the proteins on the outer surface of the liposome. Phospholipids having unnatural stereochemistry may be prepared as described in the literature, for example see, (J. A. Virtanen et. al., Chem. Phys. Lipids 27 (1980) 185). D-Mannitol is tritylated to yield 1,6-ditrityl-D-mannitol, which is oxidized with lead tetra-acetate and the product reduced with sodium borohydride to yield 1-trityl-sn-glycerol (1-TrG). Diacylglycerols and phospholipids can be prepared starting from 1-TrG by standard methods. For the liposomes described in this application ether bond is preferred at least in the primary hydroxyl group, because it is resistant against lipase. In some embodiments an sn-hydroxyl ester bond may be useful because the unnatural stereochemistry makes this bond stable against phospholipase $A_2$. Other lipids for use in the subject liposomes include 2-oleoyl-3-triacontanyl-sn-glycero-1phosphatidyl ethanolamine and other 2-acyl-2-alkyl-PE's.

In another embodiment of the binding molecule-multienzyme complexes of the invention, in which the joining component is a peptide. The peptide may be either naturally occurring, e.g., spectrin or fibrin, or may be artificial. The peptide joining component may take the form of a large fusion protein when the binding effector molecule and the therapeutic effector molecule are both proteins. One advantage of using binding molecule-multienzyme complexes that are fusion proteins is that the compound may be produced by standard recombinant DNA production techniques such as those known to the person of ordinary skill in the art, such as described in Goedolel, *Gene Expression Technology Methods in Enzymology*, Vol. 85 Academic Press, San Diego (1988). In other embodiments of the invention peptide joining components may be used in which the compound is not a fusion protein.

In other embodiments of the invention, the joining component may be a dendrimer. A dendrimer is a highly branched polymer. Dendrimers provide numerous sites of attachment for effector molecules at the termini of the dendrimer. Information on how to synthesize various dendrimers suitable for use in conjunction with this invention are well known to the person of ordinary skill in the art of organic chemistry. Enzymes may be conjugated with polymers to extend their half-life in the blood (R. F. Sherwood et. al., Biochem J. 164 (1977) 461); M. J. Knauf, et. al., *J. Biol. Chem.* 263 (1988) 15064; A. Abuchowski and F. Davis in *"Enzymes as Drugs"* (Eds. J. Holsenberg and J. Roberts) John Wiley and Sons, New York, 1981, pp. 367–383). Description of how to join effector molecules to polymers can be found in R. Labeque, et. al., *Proc. Natl Acad. Sci. USA* 90 (1993) 3476 (Phospholipase A2 for hypercholesterolemia treatment). The structure of the polymer is not well defined and the coupling is even less defined. Only average number of the enzyme molecules per enzyme is known. The coupling of the enzyme occur typically via lysine residues and because most enzymes contain several lysines, the polymer can be coupled to any of these and possible to several lysines in the same enzyme.

The effector molecules can be chemically coupled with a polymer, which can be an artificial or a biopolymer. Craft polymers give the highest operational freedom. Dendrimers having chemically different branches can provide chemically well defined structure.

The binding molecule-multienzyme complexes of the invention may be produced in a variety of environments, either in vitro or in vivo. Binding molecule-multienzyme complexes may be constructed in vitro by mixing the various constituents under conditions. Conditions in the in vitro reaction mixture may be varied so as to influence the rate of binding molecule-multienzyme complexes formation and the nature of the binding molecule-multienzyme complexes produced.

The binding molecule-multienzyme complexes of the present invention may be used in a very wide variety of applications which include, but are not limited to treatment of infectious disease, including HIV-1 infections, treatment of atherosclerosis, treatment of cancer, immunoassays, self-assembling resist materials, for electronic self-assembling nanocircuitry, catalytic clusters, sensors, supramolecular drugs, which are capable of encapsulating viruses and/or destroying viruses. Drug and enzyme targeting to cells and viruses may be enormously improved by using supramolecular assemblies of the invention comprising many similar or different monoclonal antibodies and several drug molecules, enzymes or other effector molecules.

It will be appreciated by the person of ordinary skill in the art that the therapeutic embodiments of the binding molecule-multienzyme complexes of the invention (e.g., compound for the treatment of cancer, viral infections, atherosclerosis) also include compounds in which effector molecules are joined to one another through conventional, i.e., non-polynucleotide, linkers. The use of non-polynucleotide linkers is well known the person of ordinary skill in the art and is described in, among other places, in several volumes of the series Methods in Enzymology, Academic Press, San Diego Calif. Examples of such non-polynucleotide linkers include, 4-benzoylbenzoic Acid N-hydroxysuccinimide esters, 3-maleimidobenzoic acid N-hydroxysuccinimide esters, 1,4-phenyleneisothiocyanates, and the like. In those embodiments of the invention in which non-polynucleotide linkers are used to join effector molecules, it may be advantageous to administer a mixture of different effector molecule conjugates to a patient rather than a large supramolecule. In the treatment of HIV-1 infection for example, rather than administer a single supramolecule comprising (i) an anti-gp120 macromolecule, (ii) a phospholipase, and (iii) a proteinase, it may be desirable to administer a formulation comprising (i) an anti-gp120-phospholipase conjugate and (ii) an anti-gp120-protease conjugate.

When the binding molecule-multienzyme complexes of the invention are used in vivo, the compounds are typically administered in a composition comprising a pharmaceutical carrier. A pharmaceutical carrier can be any compatible, non-toxic substance suitable for delivery of the therapeutic proteins and nucleic acids to the patient. Sterile water, alcohol, fats, waxes, and inert solids may be included in the carrier. Pharmaceutically accepted adjuvants (buffering agents, dispersing agent) may also be incorporated into the pharmaceutical composition.

The binding molecule-multienzyme complexes components of the invention may be administered to a patient in a variety of ways. Preferably, the pharmaceutical compositions may be administered parenterally, i.e., subcutaneously, intramuscularly or intravenously. Thus, this invention provides compositions for parenteral administration which comprise a solution of the human monoclonal antibody or a cocktail thereof dissolved in an acceptable carrier, preferably an aqueous carrier. A variety of aqueous carriers can be used, e.g., water, buffered water, 0.4% saline, 0.3% glycerine and the like. These solutions are sterile and generally free of particulate matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate, etc. The concentration of antibody in these formulations can vary widely, e.g., from less than about 0.5%, usually at or at least about 1% to as much as 15 or 20% by weight and will be selected primarily based on fluid volumes, viscosities, etc., in accordance with the particular mode of administration selected.

Actual methods for preparing parenterally administrable compositions and adjustments necessary for administration to subjects will be known or apparent to those skilled in the art and are described in more detail in, for example, *Remington's Pharmaceutical Science*, 15th Ed., Mack Publishing Company, Easton, Pa. (1980), which is incorporated herein by reference.

An important use of some of the embodiments of supramolecules of the invention is a 2-dimensional supramolecular structures on semiconductor or other electrically conductive surfaces so that desired patterns of self-assembling resist materials may be conveniently formed. Thus, the use of X-rays and electron beam lithography may be avoided when creating nanometerscale patterns on the semiconductor surfaces. This capability will make a completely new order of nanoelectronics possible.

A second application of major importance will be self-assembling nanocircuitry using this technique. Pre-prepared diodes, transistors, capacitors, resistors, etc. and wires can be connected in highly selective ways to form two or three dimensional electronic entities. Electronically conducting complementary polynucleotide chains may be used when electric contact of the nanocomponents is needed.

Binding molecule-multienzyme complexes, of the invention may also be used in catalytic and sensor applications. Employing the binding molecule-multienzyme complexes methodology of the present invention, enzymes may be attached to a surface in an organized fashion in order to create desired sequential reaction. With regard to sensor applications, a sensor may be created that contains additional biomolecules or organic molecules that give a photonic or electrical signal when a molecule of interest is the supermolecular assembly sensor.

Binding molecule-multienzyme complexes components of the invention may be used to provide novel immunoassays and related assays for the detection of compounds of interest. Immunoassay technology is highly developed and well known to person of ordinary skill in the art, see, for example, Hudson, *Practical Immunoloqy 3rd Ed.* Oxford Publication (1989), and Catty *Antibodies: A Practical Approach Volumes* 1 & 2 Oxford University press (1989). Conventional immunoassays typically employ antibodies conjugated to enzymes, and/or antibody-antibody conjugates. It will be appreciated by one skilled in the art that many embodiments of the binding molecule-multienzyme complexes, preferably the supramolecular assemblies may be substituted for the conventional antibody conjugates used in conventional assays. Binding molecule-multienzyme complexes of the invention useful or assay comprise at least one member of a specific binding pair (e.g., an antibody, where the specific binding pair of molecules is an antibody and antigen target) as an effector molecule portion of a binding molecule-multienzyme complexes component. Such binding molecule-multienzyme complexes supramolecules may, for example comprise (1) two or more specific binding pair members, e.g., antibodies, (2) an antibody and an enzyme capable of generating a detectable signal, e.g., alkaline phosphatase.

Numerous advantageous variants of conventional immunoassays are enabled by employing the binding molecule multi-enzyme complexes, preferably supramolecular assemblies of invention instead of conventional antibody conjugates because certain embodiments of the subject binding molecule-multienzyme complexes may be assembled, disassembled, or reassembled during an assay due to the ability of the double-stranded nucleic acid moieties of the assembly to disassociate or removal of the appropriate conditions. For example, (i) a binding molecule-multienzyme complexes comprising antibody joined by a double stranded nucleic acid molecule to an enzyme producing a detectable signal may be bound to a target antigen of interest, (ii) the binding molecule-multienzyme complexes may then be disassociated so as to release the binding molecule-multienzyme complexes comprising the enzyme effector molecule (iii) the bound portion of the binding molecule-multienzyme complexes may then be used to form a new binding molecule-multienzyme complexes with a second antibody as an effector molecule, thereby permitting the immobilization of a second molecule of interest at the same location as the bound binding molecule-multienzyme complexes portion. A person of ordinary skill in the art will appreciate that the properties the subject binding molecule-multienzyme complexes structures permit many new and useful assay procedures to be performed.

The binding molecule-multienzyme complexes of the invention may be adapted so as to prevent or treat various infectious diseases, including HIV-1, the etiological agent of AIDS. Specific infectious organisms may be targeted by creating, and administering in an effective amount of binding molecule-multienzyme complexes of the invention comprising as therapeutic effector molecules, (1) an antibody specific for molecule on the infections agent and (2) an enzyme capable of catalyzing the modification of some integral structure of the infectious agent. For example, a binding molecule-multienzyme complexes adapted for the control of HIV-1 may comprise an antibody specific for one or more HIV-1 virus components, e.g., gp120, and one or more of the following enzymes (1) a phospholipase $A_2$, (2) a lipase, (3) a cholesterol esterase. By including such enzymes in a binding molecule-multienzyme complexes, the lipid bilayer coat the infectious viral particle that may be destroyed. Additionally, binding molecule-multienzyme complexes of the invention adapted for the treatment of the infectious disease may further comprise of protease capable of degrading a protein component of the infectious agent and/or a single stranded nucleic acid capable of hybridizing to a portion of the genome of the infectious organism of interest. In other embodiments of the binding molecule-multienzyme complexes of the invention for the treatment/prevention of HIV-1 infections, soluble CD4 (e.g., TT4) may be used as a binding effector molecule to provide viral target specificity. Soluble CD4 (sCD4) fragment of CD4 binds to the HIV-1 virus in a manner similar to the binding of whole CD4 (R. Fisher, et. al. *Nature* 331 (1988) 76–78). The production of sCD4 is described among other places in, P. Maddon, et. al., U.S. Pat. No. 5,126,433. In order to provide for the covalent attachement of sCD4 to the remainder of the binding molecule-multienzyme complex, one ore more cysteine residue may be added to the sCD4 (or CD4) by mutation. Preferably, the additional cysteine residues are located on side of the CD4 fragment that is distal to the HIV-1 binding site; preferred sites for introducing cysteine residue substitution mutations are at sCD4 amino acid residue positions 64, 364 or 374 or 377. sCD4 containing additional cysteine residues may be produced either by in vitro peptide synthesis techniques or by conventional recombinant DNA expression techniques.

Binding molecule-multienzyme complexes, particularly embodiments employing a liposome as a joining component, may be adapted for the treatment of atherosclerosis. LDL has a cholesterol and cholesterol ester core surrounded by a phospholipid layer. Into the spherical lipid droplet four apo B molecules are partially buried and are tetrahedrally located. The overall structure is well defined and proteins are oriented so that the lipophilic domain is inside the lipid and hydrophilic part is in the water. LDL is very sensitive and forms by vortexin, in vitro similar deposits as observed in atherosclerotic plaque (J. C. Khoo, E. Miller, P. McLoughlin and D. Steinberg. 1988. Enchanced Macrophage Uptake of Low Density Lipoprotein after Self-Aggregation. Arteriosclerosis 8: 348–358). The lipid part and apolipoprotein B are separated and most of the protein is denatured and deposited. Lipids from several LDL particles aggregate and form droplets having diameters of 30–400 nm. An antibody which is specific for the denatured LDL can be produced by a person of ordinary skill in the art. The heterogeneity of the plaque can be largely circumvented by the use of liposomal binding molecule-multienzyme complexes. Furthermore, because liposome binding molecule-multienzyme complexes binding is mediated by multiple antibodies, it is much stronger and more selective than the binding by a single antibody. Up to 50–60 antibodies can bind the liposome to the plaque without preventing enzymatic reaction. When lipid carbon-carbon double bonds in LDL are oxidized to aldehydes they form Schiff's bases with the lysines of apolipoprotein B (W. Palinski in "Cell Interactions in Atherosclerosis" (Eds. N. J. Severs and H. Robenek), CRC Press, Boca Raton, 1992, p. 1.). These structures in oxidized LDL are antigenic and may used as targets for antibodies to be used as effector molecules, both binding effector molecules and therapeutic effector molecules. Because this reaction proceeds often many years in the plaque, the concentration of the antigens is high in contrary to circulating LDL particles, which are metabolized fast. Significant part of the oxidation is performed by the metalloproteins secreted by macrophages. Unfortunately macrophages are located mainly close to the edge of the plaque and the plaque is not evenly oxidized. Accordingly antibody to oxidized LDL does not bind evenly to the plaque. The enzymes coupled to the antibody would digest mainly the edges of the plaque thereby amplifying the effect of macrophages. The end result might be the rupture of the plaque.

Another possibility is to use an antibody that is even moderately specific for plaque to place oxidizing enzymes near deposited LDL. Circulating LDL might also be oxidized to some degree, but it is metabolized fast and completely removed in a relatively short period of time. Antibody-multienzyme complex containing antibody for oxidized LDL and digestive enzymes is then given to the patient. Oxidized LDL is now evenly distributed and the plaque is also digested evenly. Thus, one treatment cycle consists of series administration of both the oxidative and the digestive antibody-enzyme complexes. A chimeric human/murine antibody Z2D3 specific for human atheroma has been prepared (J. Narula, C. Ditlow, F. Chen, H. W. Strauss and B.-A. Khaw. 1992. Non-invasive localization of experimental atherosclerotic lesions with murine/human chimeric antibody Z2D3 F(ab')$_2$. American Heart Association 66th Scientific Meeting, Nov. 16–19, 1992) an may be used as effector molecule in the binding molecule-multienzyme complexes of the invention. Fibrin is a major noncellular constituent of atherosclerotic plaque. Fibrin is insoluble even, if the surrounding lipids are removed. Fibrin network will also hold the cells immobilized. Accordingly the digestion of fibrin is mandatory. Plasmin is natural fibrin hydrolase and is preferred also in this connection. The problem with several active proteases is that they are inhibited in the blood and removed from the circulation. Obvious method to avoid fast removal is to use plasminogen, which can be activated after the liposome has attached onto the plaque. Activation can be performed using, for instance, urokinase or recombinant tissue plasminogen activator. These two proteins are already clinically approved for the treatment of acute myocardial infarction. They can be used as such or targeted using separate liposomes. Using liposomes the enzymatic activity is released only if two different types of liposomes are simultaneously present. The selectivity is increased enormously, because only a relatively large surface containing enough antigens can bind these two liposomes simultaneously. For instance, circulating lipoprotein particles will not be affected. Side effects are reduced, because freely floating liposome does not have proteolytic activity. The principle of using inactive proenzyme can be extended to phospholipase subscript, which has also an inactive proenzyme. The use of proenzymes is not only advantageous for the clinical use, but also the production of proenzymes is much easier than the production of actual enzymes. The presence of active phospholipase A$_2$ would be virtually impossible in the goat milk, while proenzyme is harmless. Cholesterol esters and triglycerides are most insoluble lipid components. By hydrolyzing them by cholesterol ester hydrolase and lipase will produce relatively easily soluble fatty acids and monoglycerides. Cholesterol is the largest lipophilic component. Moreover it is the most difficult to degrade. Cholesterol oxidase will transform cholesterol to 4-cholester-3-one, which is relatively polar. Thus oxidized cholesterol should be removed from the plaque.

The principles presented in this application enable the purposeful construction of huge molecular assemblies having an exactly known chemical structure. For example, in Example 6, as shown in FIGS. 5A–D, describes the construction of a supramolecule for capturing virus particles which would have a molecular weight of about 4,000,000 Daltons.

Figure 15A:
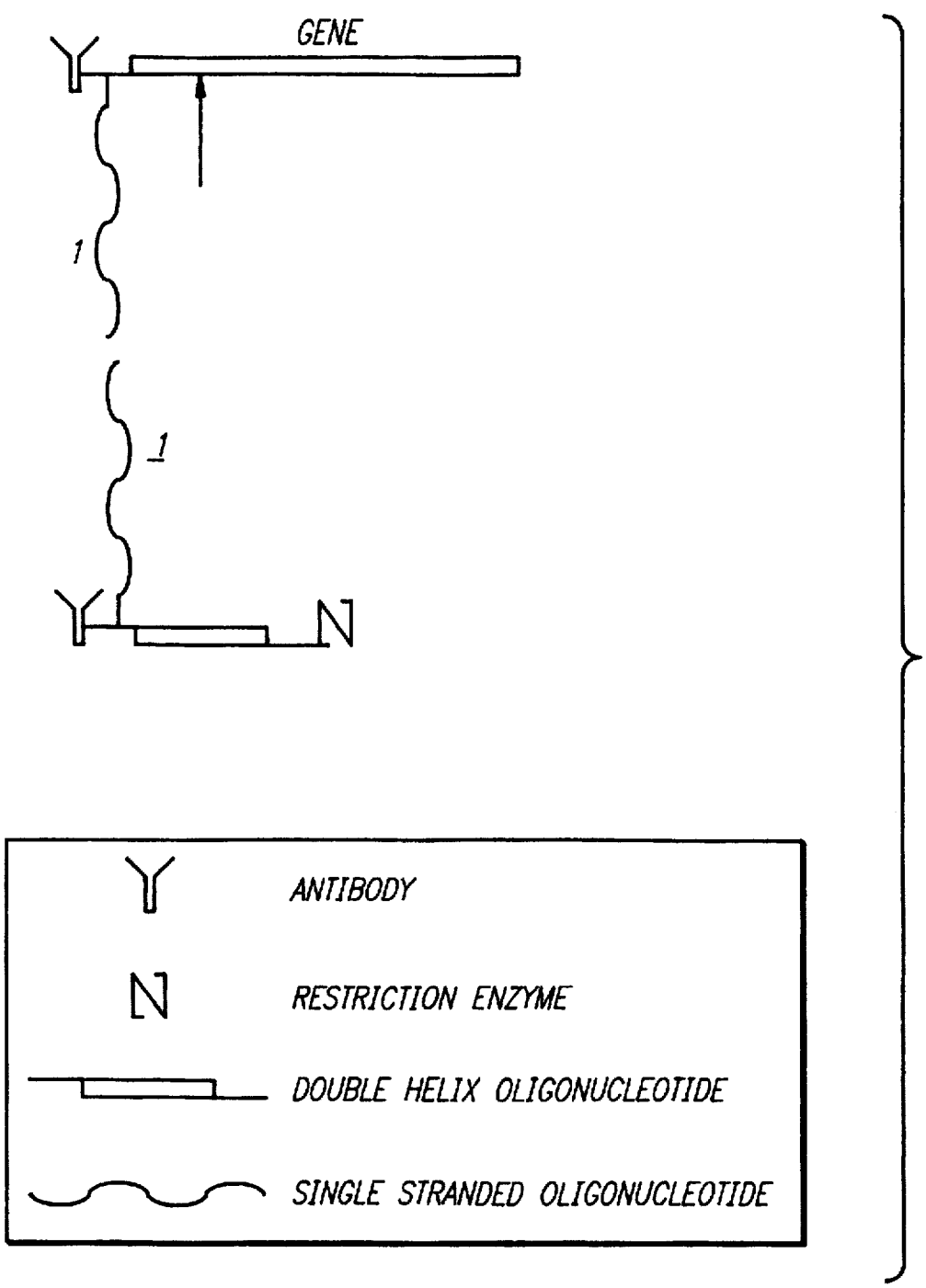
FIG. 15A is a schematic representation of a supramolecule adapted for transformation of a nucleic acid of interest into a eukaryotic cell.
Figure 15B:
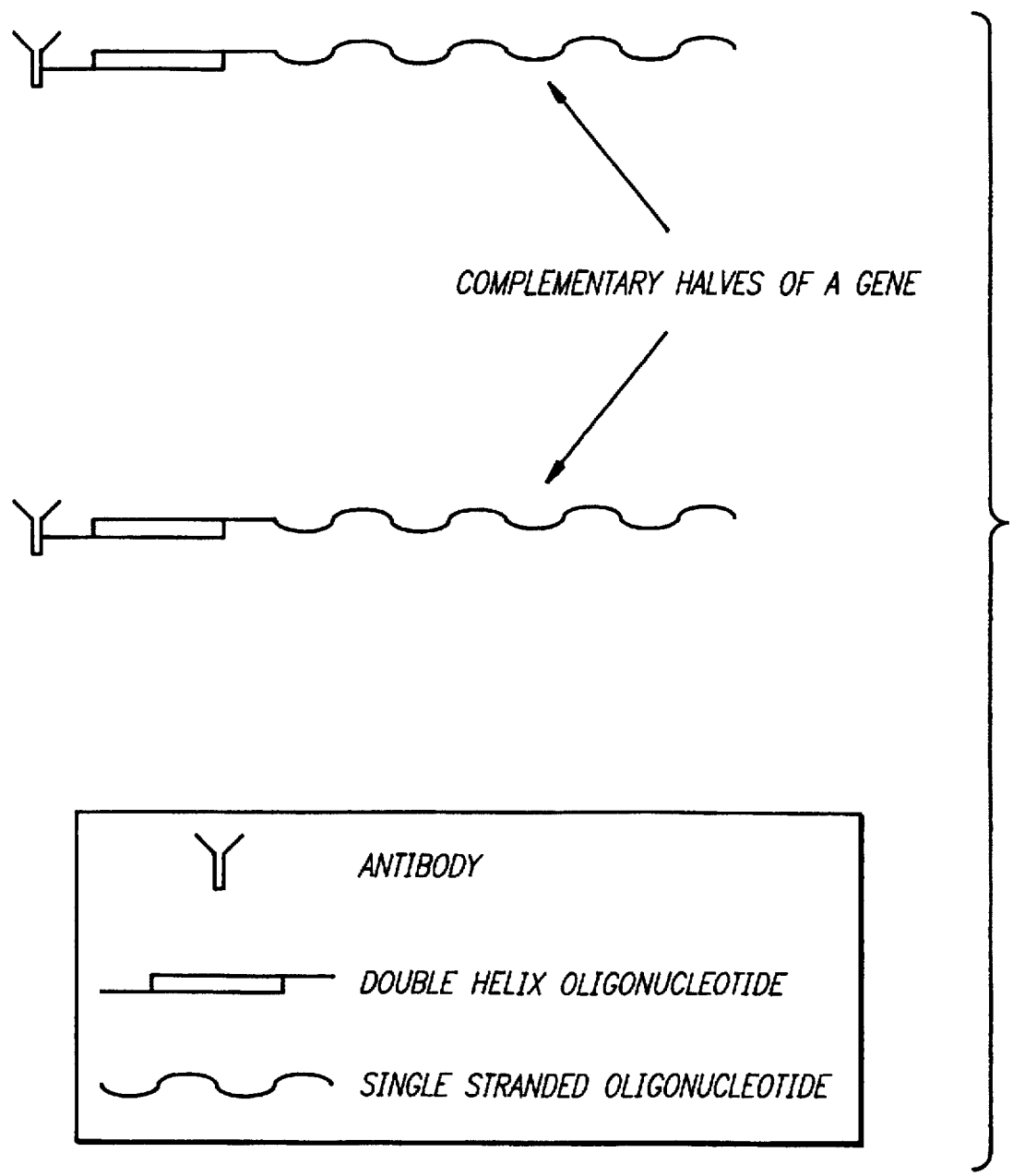
FIG. 15B is a schematic representation of a supramolecule adapted for transformation into a cell.
Figure 15C:
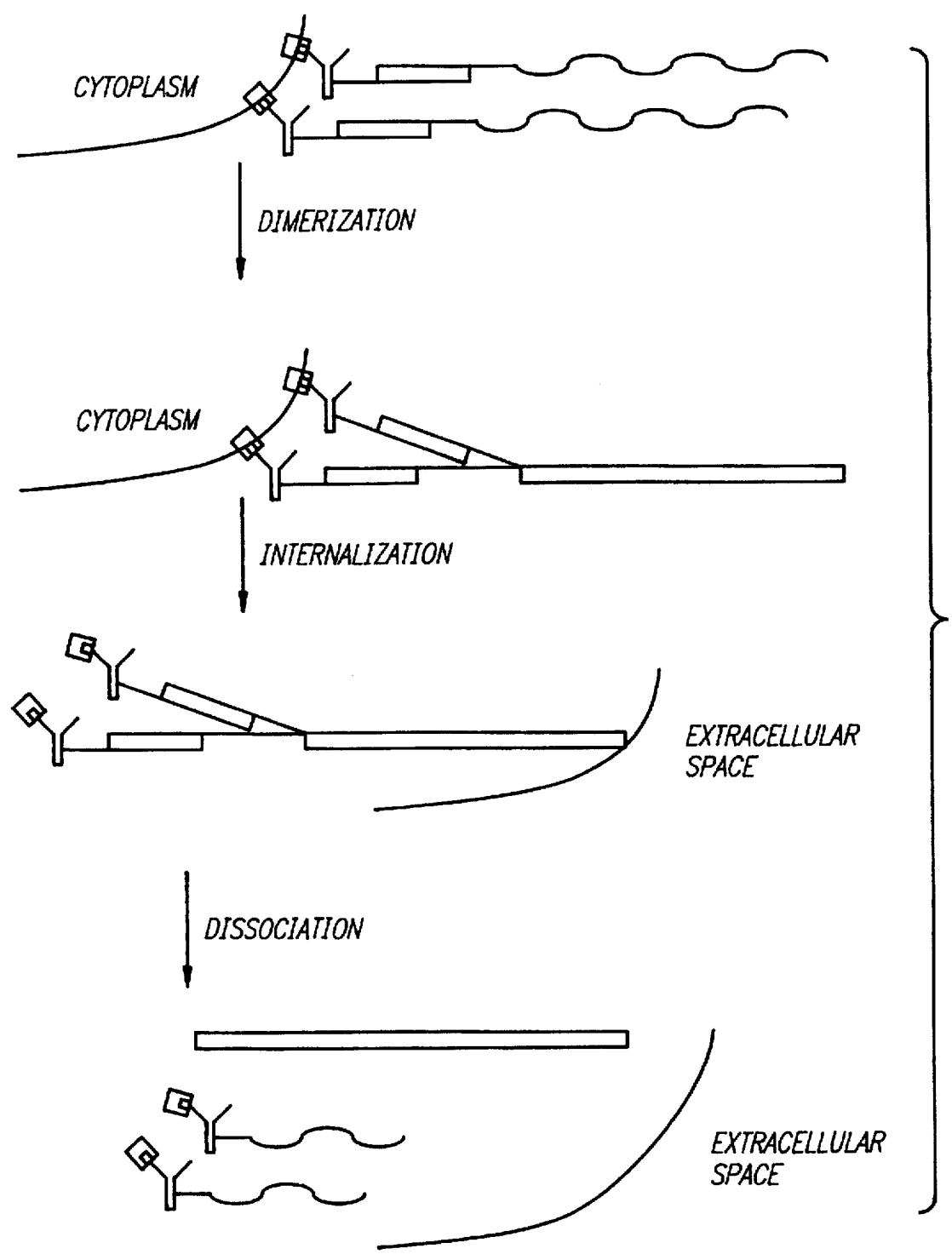
FIG. 15C is a schematic representation of a supramolecule adapted for transforming a cell and the internalization, i.e., transformation process.
Figure 16:
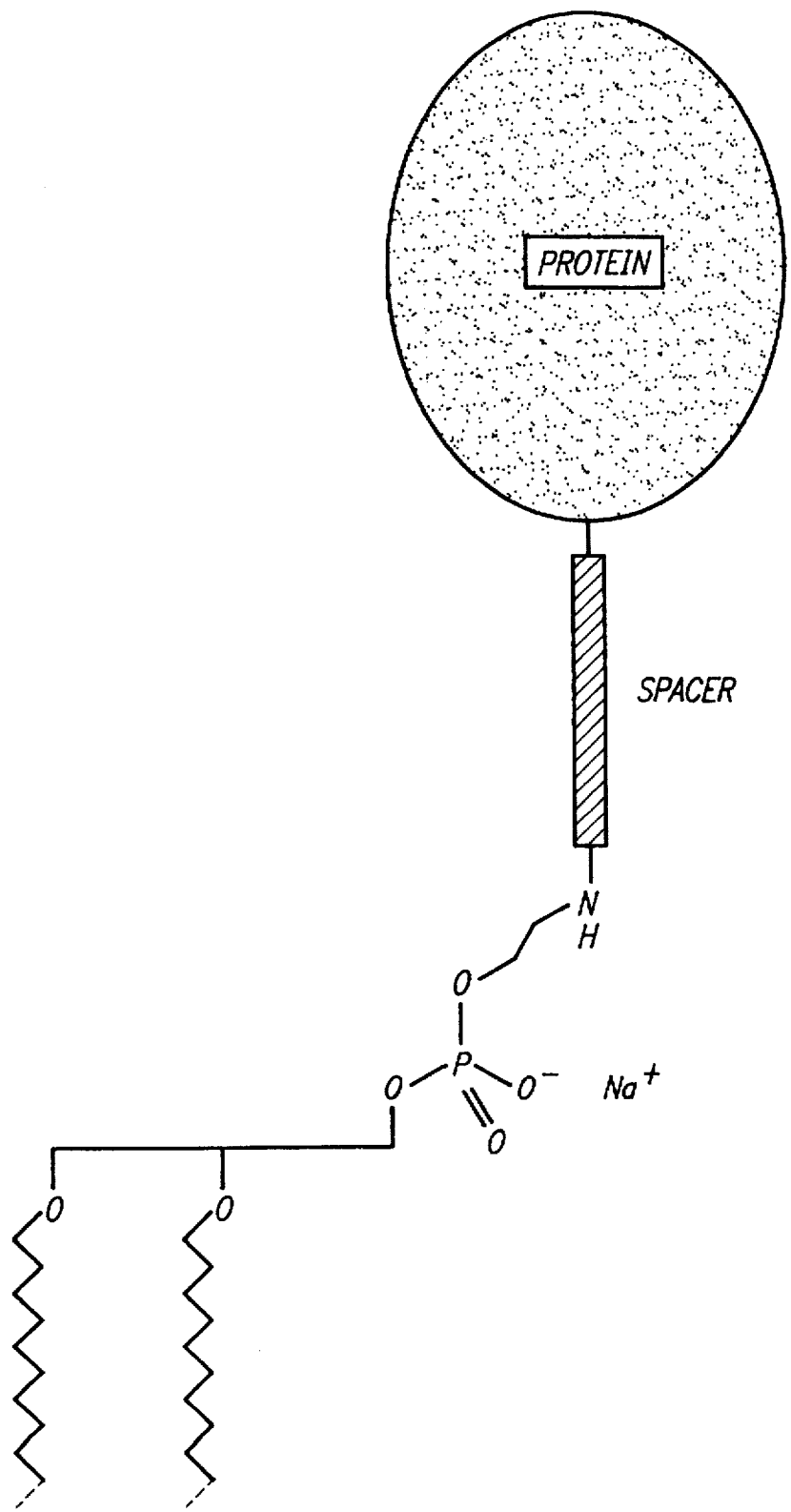
FIG. 16 is a schematic diagram of proteinaceous effector molecule covalently coupled to a phospholipid which may be incorporated into the binding molecule-multienzyme complexes of the invention.
Figure 17:
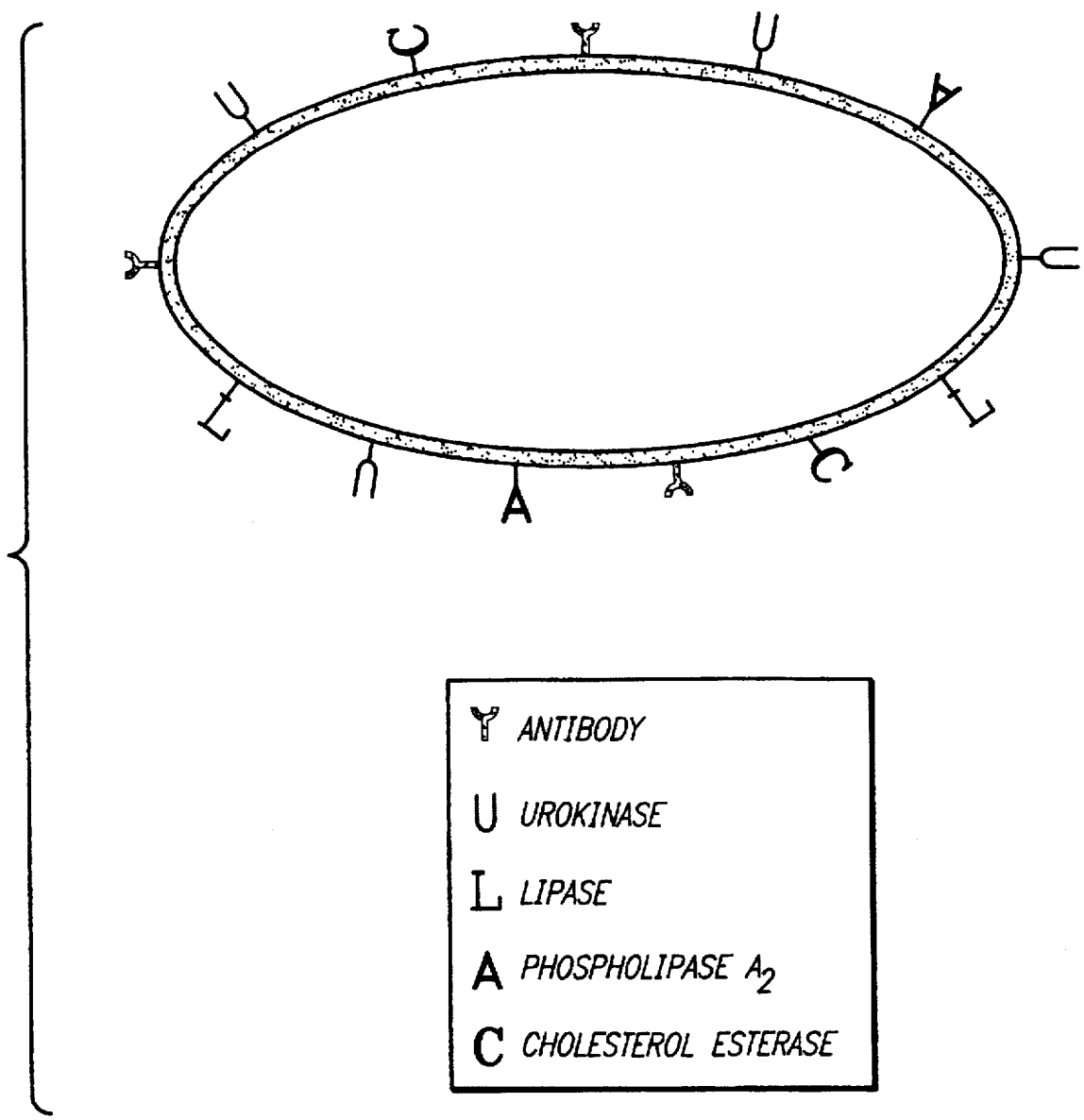
FIG. 17 is a schematic diagram of liposomal binding molecule-multienzyme complex of the invention adapted for use in treating atherosclerosis. The liposomal binding molecule-multienzyme complex comprises antibodies an binding effector molecules and lipase, urokinase, phospholipase $A_2$, and cholesterol esterase as therapeutic effector molecules.
Figure 18:
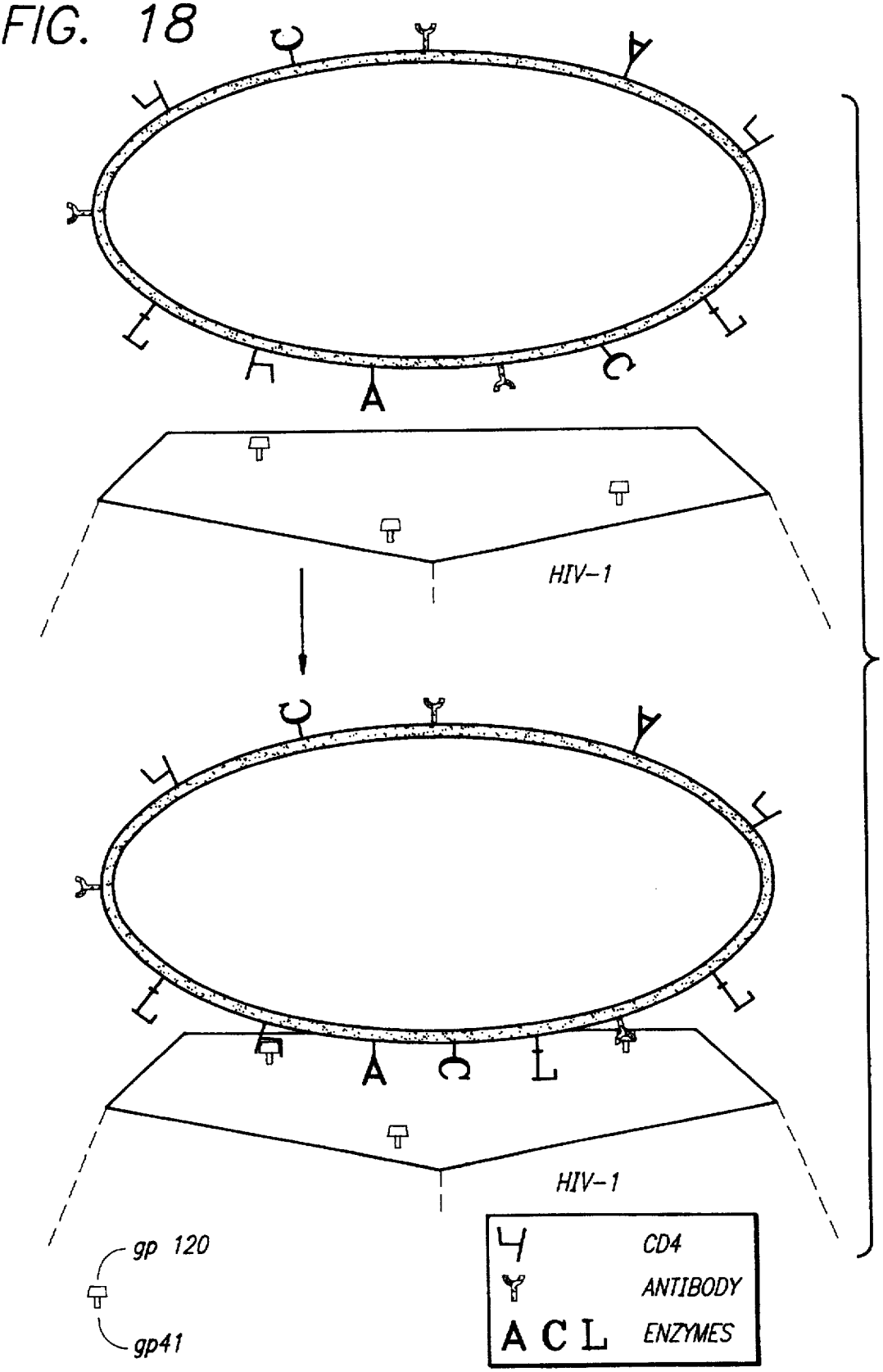
FIG. 18 is a schematic diagram of liposomal binding molecule-multienzyme complex of the invention adapted for use in treating HIV-1 infections and the interaction of the complex within an HIV-1 virion. Diffusion of the effector molecules in the liposome are demonstrated. The symbol "A" refers to phospholipase $A_2$ used as a therapeutic effector molecule. The symbol "C" refers to cholesterol esterase used as a therapeutic effector molecule. The symbol "L" refers to lipase used as a therapeutic effector molecule.

Another aspect of the invention is to provide binding molecule-multienzyme complexes adapted so as to mediate the transfer of polynucleotides of interest into a host cell, i.e., transfection or transformation. Binding molecule-multienzyme complexes of the invention for cell transfection comprise effect of molecules capable of initiation the natural internalization machinery of a eukaryotic cell. Such effector molecules e.g., antibodies, are capable of binding to cell surface molecules, e.g., receptors, and preferably cross-linking the receptors when the effector molecules are components of a binding molecule-multienzyme complexes of the invention. A binding molecule-multi-enzyme complexes comprising multiple antibodies may increase chances of internalization by increasing the concentration of cross-linked cell-surface molecules. Additionally, sets of supramolecular components of the invention may be used to transform cells by employing the internalization machinery of the cell. For example, a first supramolecular component consisting of a cell surface receptor specific antibody joined to a nucleic acid moiety and a second supramolecular component consisting of a second cell surface receptor-specific antibody joined to a complementary nucleic acid moiety. By permitting the first and second supramolecular component nucleic acids to hybridize to one another after the antibody moieties have bound to a cell surface, receptor cross-linking, and hence internalization, may be achieved. Supramolecular assemblies of the invention may also comprise additional nucleic acids for internalization into a host cell of interest. Nucleic acid components of supramolecular assemblies for cell transformation may be detached from the supramolecular assembly in a variety of ways. As shown in FIG. 15A, the nucleic acid may be detached through the use of restriction enzymes or other nucleases. Additionally, nucleic acid components may detach from binding molecule-multienzyme complexes through the process of nucleic acid denaturalization, provided the nucleic acids are not covalently attached to the assembly. In another embodiment of the subject binding molecule-multienzyme complexes for transformation, effector molecules having phospholipase A$_2$ activity may be used to introduce pores into a cell membrane. In other embodiments of the invention, the supramolecular assembly may comprise polyamines, e.g., spermine so as to mediate transformation.

The large scale solid phase synthesis (e.g., over 1 mmole) of oligonucleotides is difficult to achieve using previously described synthesis methods. A significant problem with large scale synthesis is the efficient mixing of the heterogeneous system. Silica, polystyrene or other similar solid support particles (typically spherical) modified with polyethyleneoxide chains are commonly used as a support for oligonucleotide synthesis. The growing oligonucleotide chains may form coils and stacking relationships, even between oligonulceotides on separate support particles, thereby creating a network that can prevent the efficient entry of reagents. The higher density of these spherical particles also makes efficient reaction mixing even more difficult.

Large scale synthesis of oligonucleotide, e.g., 0.1–1 mole, is useful for the commercial scale production of supramolecules and supramolecular components of the invention. The following improvements of the current oligonucleotide synthesis procedure solve the above-described problems surrounding large scale synthesis of oligonucleotides. First, acetonitrile is replaced with a solvent or solvent mixture that has a specific density of about one and that is also better able to solvate the heterocyclic bases of nucleotides than acetonitrile. Suitable solvents having these desired properties include benzonitrile or a mixture of acetonitrile and dichlorobenzene. The density of these solvents is compatible with the use of polystyrene or comparable solid supports. Solid supports will float in these preferred solvents, thereby permitting mixing steps to be easily performed. Another improvement over conventional oligonucleotide synthesis that may be used to effect large scale synthesis is the exposure of the reaction mixture to microwaves during the coupling step. Microwaves increase molecular rotation and reduce unwanted polynucleotide network formation without subjecting the reaction mixture to excessive heat. An additional improvement over conventional oligonucleotide methods synthesis is instead of monomeric amidires, dimeric or trimeric amidites may be used as building blocks. Even larger amidite multimers may be used to construct oligonucleotides; however, monomeric, dimeric and trimeric amidites and their combinations are preferred. Using dimers and trimers as building blocks requires preparation of 16 dimer amidites and up to 64 trimer amidires separate. The use of multimeric amidires the number of couplings during automated synthesis is decreased significantly and accordingly the yield and purity is increased. The three above-described oligonucleotide improvements may be employed separately or in combination with one another. A person of ordinary skill in the art will appreciate that an ideal combination of the above-described improvements will depend upon the length of the oligonucleotide described and the scale of the synthesis.

The invention having been described above may be better understood by reference to the following examples. The following examples are offered in order to illustrate the invention and should not be interpreted as limiting the invention

EXAMPLES

1. Illustration of Complementary Nucleic Acid Sequences

Table 1 provides examples of nucleic acid sequences and their complementary sequences that may be used in the present invention; the construction of complementary nucleic acids is known to the person of ordinary skill in the art.

For the purpose of these examples, complementary chains of nucleic acids are depicted as an integer and that integer underlined. For example, $-(A_n-C_p)_i$ is identified as 1 in Table 1. Its complement, $-(T_n-G_p)_i$ is labelled $\underline{1}$. With regard to the indices n, p, q and r used in Table 1, it should be understood that these indices are independent for each set of complementary nucleic acid chains.

TABLE 1

| Chain Unit | Complementary Unit | Complementary | Chain |
|---|---|---|---|
| 1 | $-(A_n-C_p)i$ | $(T_n-G_p)i-$ | | 1 |
| 2 | $-(A_n-T_p)i$ | $(T_n-A_p)i-$ | $n \neq p^a$ | 2 |
| 3 | $-(C_n-G_p)i$ | $(G_n-C_p)i-$ | $n \neq p^a$ | 3 |
| 4 | $-(A_n-C_p-G_q)j$ | $(T_n-G_p-C_q)j-$ | | 4 |
| 5 | $-(A_n-G_p-C_q)j$ | $(T_n-C_p-G_q)j-$ | | 5 |
| 6 | $-(A_n-C_p-T_q)j$ | $(T_n-G_p-A_q)j-$ | | 6 |

TABLE 1-continued

| Chain Unit | Complementary Unit | Complementary | Chain |
|---|---|---|---|
| 7 | $-(A_n-T_p-C_q)j$ | $(T_n-A_p-G_q)j-$ | | 7 |
| 8 | $-(A_n-C_p-A_q-G_r)j$ | $(T_n-G_p-T_q-C_r)j-$ | | 8 |
| 9 | $-(A_n-G_p-A_q-C_r)j$ | $(T_n-C_p-T_q-G_r)j-$ | | 9 |

[a]If n = p then the oligonucleotide is self-complementary and can be useful when similar units are coupled together.

Many of the examples given herein are provided in order to demonstrate the principles of the invention. Preferably, repeating units are avoided.

DNA and RNA triple helices are also well known and may be used to form the supramolecular assemblies of the invention. Triple helices may result from the association between T...A...T and C...G...C. As a result, nucleic acid changes, such as those listed in Table 2 can be used to form triple helices to bind different components of a supramolecule. One advantage in using triple helix structures is increased rigidity. This property can be utilized even after the supramolecule has been assembled. Triple helix forming oligonucleotides may be used as the nucleic acid moieties of the supramolecular components of the invention. Double helical structures, which are capable of binding to a third oligonucleotide, do so and give rigidity and shape to the supramolecule. The use of triple helices in supramolecular assemblies is demonstrated in FIG. 8.

TABLE 2

| | Center coil | Two outer coils |
|---|---|---|
| 11 | $-A_h$ | $T_h-$ |
| 12 | $-G_h$ | $C_h-$ |
| 13 | $-(A_n-G_p)i$ | $(T_n-C_p)i-$ |
| 14 | $-(A_n-A_p-G_q)j$ | $(T_n-T_p-C_q)j-$ |
| 15 | $-(A_n-G_p-G_q)j$ | $(T_n-C_p-C_q)j-$ |

2. Construction of a Square Planar Supramolecule

FIG. 2(A) depicts the construction of a square planar supramolecule from four different components. Component A comprises effector molecule M to which is attached nucleic acid chains 1 and 2. Component B is formed by attaching nucleic acid chains $\underline{1}$ and 3 to effector molecule N. Component C is formed by attaching nucleic acid chains $\underline{2}$ and 3 to effector molecule P. Component D is formed by attaching two nucleic acid chains $\underline{3}$ to effector molecule Q. When components A, B and C are mixed, the complementary chains 2 and $\underline{2}$ of components A and C bind and the complementary chains 1 and $\underline{1}$ of components A and B bind. When component D is added, the $\underline{3}$ nucleic acid chains bind to the 3 chains of components A and C to form the square supramolecule depicted in FIG. 2(A).

Figure 2B:
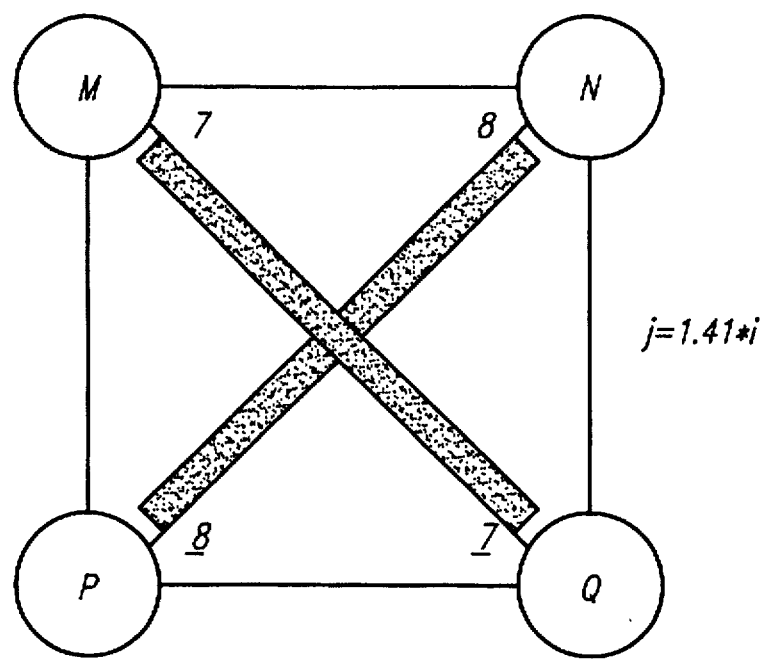
FIG. 2(B) is a schematic representation of the construction of a square planar supramolecule constructed from four components which is reenforced by diagonal double stranded nucleic acid chains.
Figure 2C:
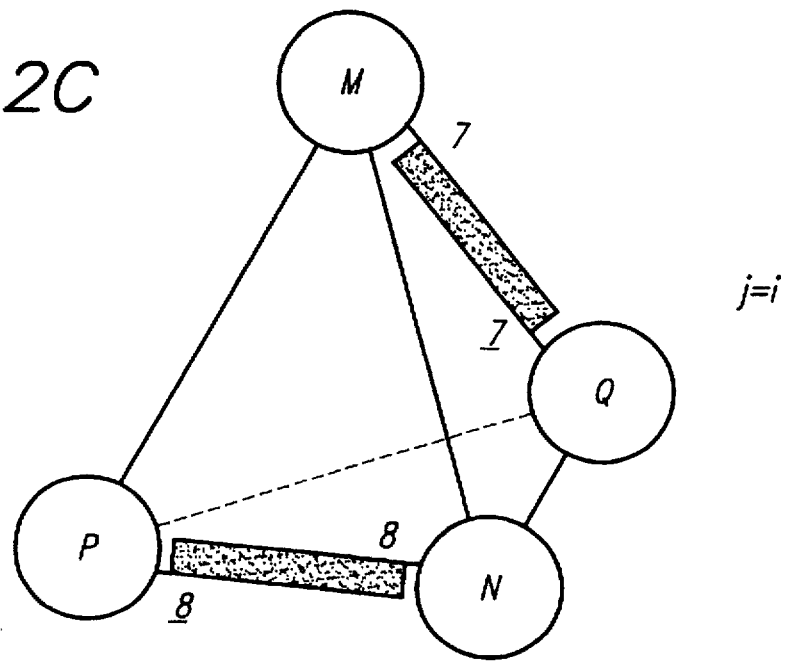
FIG. 2(C) is a schematic representation of the construction of a tetrahedral supramolecule constructed from four components.

FIG. 2(B) depicts how the square planar supramolecule can be stabilized by the addition of complementary nucleic acid chains that bind component A and C to component B to D. Since the distance between diagonally positioned effector molecules are 1.41 times the distance between effector molecules on the sides of the square supramolecule, the complementary nucleic acid chains used to bind the effector molecules diagonal to one another must be at least 1.41 times as long as the complementary nucleic acid chains binding the adjacent effector molecules in order to produce a supramolecular assembly with the desired shape.

3. Construct of a Tetrahedral Supramolecule

FIG. 2(C) depicts the construction of a tetrahedral supramolecule using four components. In order to form a tetrahedral supramolecule component A is attached to components B, C and D by complementary nucleic acid chains. Similarly, components B, C and D are attached to the components by complementary nucleic acid chains.

4. Synthesis of Components of Supramolecules

A. Preparation of Nucleic Acid Chains

Several different high yield strategies for oligonucleotide synthesis have been developed, see, for example, M. J. Gait "Oligonucleotide Synthesis, a Practical Approach", IRL Press, Oxford, 1984; J. W. Engels and E. Uhlman, "Gene Synthesis", Angew. Chem. Int. Ed. Engl. (1989) 28:716–724. These methods include the phosphate diester, phosphate triester, phosphite triester and phosphonate methods. Phosphite triester chemistry, which utilizes highly reactive phosphoramidites as starting materials is currently the most favored method of synthesis (R. L. Letsinger, J. L. Finnan, G. A. Heavner and W. B. Lunsford, "Phosphite Coupling Procedure for Generating Internucleotide Links", J. Chem. Soc. (1975) 97:3278–3279; L. J. McBride and M. H. Caruthers, "An Investigation of Several Deoxynucloeside Phosphoramidites Useful for Synthesizing Deoxyoligonucleotides", Tetrahedron Lett. (1983) 24:245–248) Oligonucleotides are most commonly prepared with automated synthesis (Beaucage, et al., Tetrahedron Lett. (1981) 22:1859–1862; U.S. Pat. No. 4,458,066). All of the known methods are applicable and will provide molecular building blocks for the supramolecular assembly principle described in this application.

Enzymatic methods for the production of oligonucleotides may also be used to synthesize the polynucleotide moieties of the supramolecular components of the invention. The polynucleotide moieties may also be produced in vivo and subsequently cleaved into complementary single strands by heating, and separated by preparative electrophoresis or chromatography.

Short oligonucleotides may be coupled together chemically or enzymatically to obtain longer oligonucleotides, see, for example (S. A. Narang, et al., Meth. Enzymol. (1979) 68:90; U.S. Pat. No. 4,356,270); N. G. Dolinnaya, N. I. Sokolova, D. T. Ashirbekova and Z. A. Shabarove, "The use of BrCN for assembling modified DNA duplexes and DNA-RNA hybrids; comparison with water soluble carbodiimide", Nucleic Acid Res. (1991) 19:3067–3072).

B. Preparation of Effector Molecules

Effector molecules, which contain aliphatic amino, dialkylamino, trialkylamino, thiol, formyl oxirane, α-halogenocarbonyl, isothicyanato or hydroxysuccinimidyl ester groups of similar, may be coupled with suitably derivatized oligonucleotides using bifunctional spacers. Effector molecules which do not contain groups mentioned above may be activated so that they contain at least one of these groups for coupling. Groups that can be activated for coupling, include: carbon-carbon double and triple bonds, halogen, carbonyl, carboxyl and hydroxyl.

The amino acid residue sequence of proteins may altered through well-known genetic engineering techniques to as to produce non-naturally occurring proteins having the desired biological functions of a corresponding naturally occurring protein, but adapted for coupling to nucleic acid moieties. For example, addition of a cysteine residue, either through substitution or inserting, may add a free thiol group for coupling to a nucleic acid moiety.

C. Attachment of Nucleic Acids to Effector Molecules

Effector molecules may be attached to nucleic acids by numerous methods, including:

1. The molecular moiety is first attached to a solid support and is used as a linker for oligonucleotide synthesis. When oligonucleotide synthesis is completed the molecular moiety is detached from the solid support so that it remains covalently coupled with the oligonucleotide. An example of this procedure is a FMOC-protected polypeptide which is first synthesized on a solid support so that it has a terminal free serine hydroxyl group. The oligonucleotide synthesis is started from this hydroxyl group.

2. Molecular moieties other than nucleotides may be incorporated inside the oligonucleotide chain during the synthesis so as to provide functional groups for coupling to nucleic acids. For example, if these molecular moieties have at least two hydroxyl groups, one of which is free and another which is protected by dimethoxytrityl group, then conventional oligonucleotide synthesis methods can be used to produce a nucleic acid that may readily be coupled to an effector molecule.

3. As a last step of the oligonucleotide synthesis a molecular moiety having a suitable functional group for coupling may be attached at the end of the oligonucleotide chain. Again, if this molecular moiety has at least one hydroxyl group, it can be attached as nucleic acid monomer. This approach is already well known in the literature 4. A molecular moiety having a suitable functional group for coupling may be attached after the oligonucleotide synthesis is completed and part or all protecting groups have been removed. Especially molecular moieties attached using methods 1–3 can contain several functional groups which are protected by orthogonal protecting groups. This allows stepwise removal of protective groups and allows regioselective attachment of new molecular moieties.

Methods of attaching enzymes to oligonucleotides that are known to the person of ordinary skill in the art may be used to produce the supramolecular components and supramolecular structures of the invention. Descriptions of such techniques can be found in, for example, Jablonski et al. Nucl. Ac. Res. 14:6115–6128 (1986), Ruth DNA 3:123 (1984), Balaguer et al. Anal. Biochem. 180:50–54 (1989), Balaguer et al. Anal. Biochem. 195: 105–110 (1991), Li et al. Nuc. Ac. Res. 15:5275–5287 (1987), Ghosh et al. Anal. Biochem. 178:43–51 (1989), Murakami et al. Nuc. Ac. Res. 14:5587–5595 (1989), and Alves et al. Anal. Biochem. 189:40–50 (1988).

In order to covalently couple an oligonucleotide with a effector molecule, the oligonucleotide must contain a functional group which has a high enough reactivity to allow specific reaction at predetermined site. This functionality can be introduced into an oligonucleotide chain during normal automated synthesis, if suitable joint molecules are used. Possible functionalities include amino, dimethylamino, thiol, oxirane and other groups, which are more reactive than functional groups in nucleotides. A different approach is to use biotin-avidin chemistry or another high affinity specific non-covalent interaction. Several means of introducing these groups have already been published in the literature. See, for example, Leary, et al., Proc. Natl. Acad. Sci. USA (1983) 80:4045; Richardson and Gumport, Nucl. Acid Res. (1983) 11:6167; Lenz and Kurz, Nucl. Acid Res. (1984) 12:3435; Meinkoth and Wahl, Anal. Biochem. (1984) 138:267; Smith, et al., Nucl. Acid Res. (1985) 13:2399, J. M. Coull, H. L. Weith and R. Bischoff, Tetrahedron Lett. (1987) 27:3991–3994; J. Haralambidis, M. Chai and G. W. Tregar, *Nucleic Acid. Res.* (1987) 15:4857–4876; B. C. F. Chu and L. E. Orgel, *Nuc. Acid Res.* (1988) 16:3671–3691. In addition to the added functionality of the oligonucleotide strand, a bifunctional spacer molecule is typically used to couple oligonucleotide and a effector molecule. Many of these spacers are well known in the literature and are commercially available.

1. Attachment of Nucleic Acids to Peptides

Figure 10:
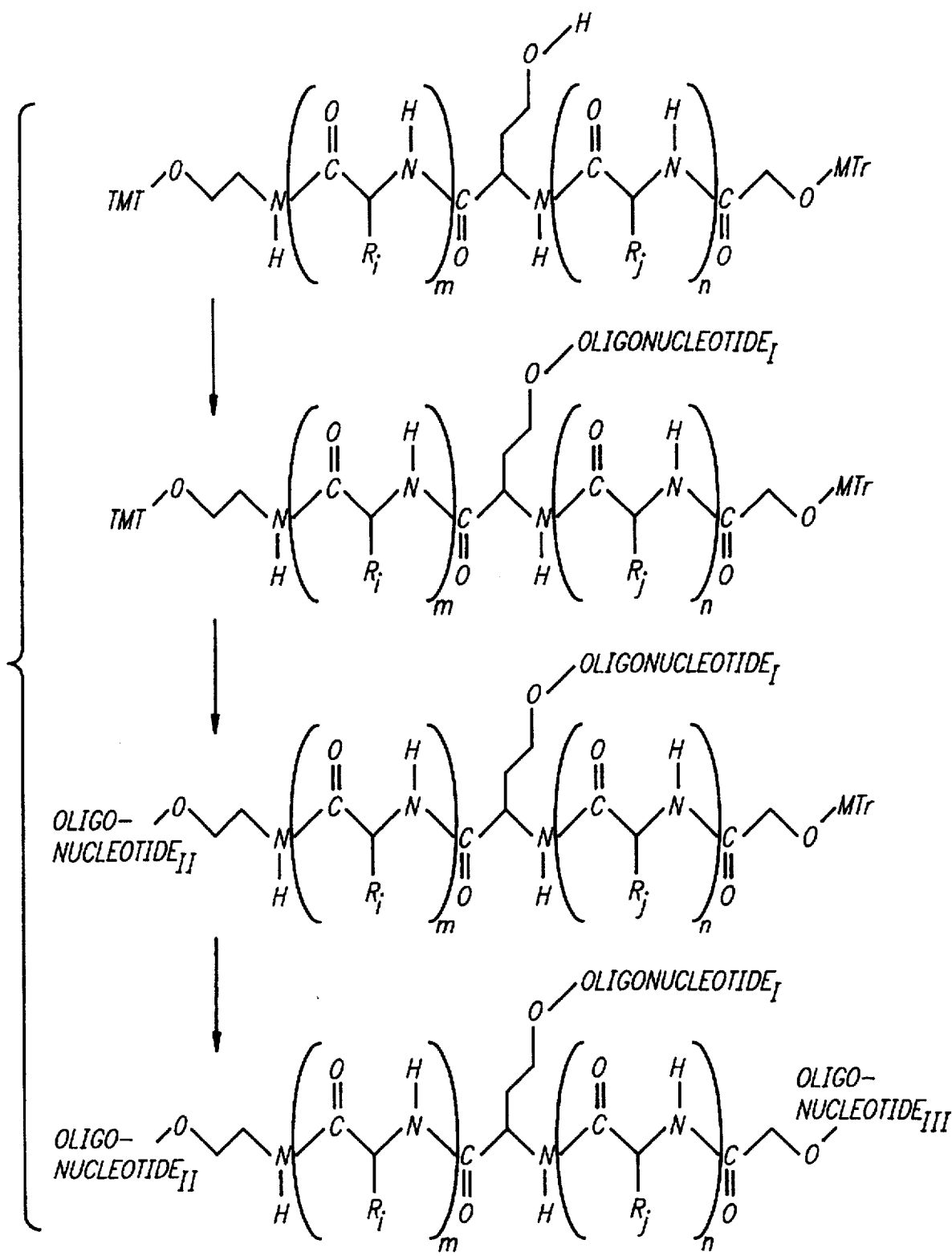
FIG. 10 illustrates an example of a spacer molecule for connecting three nucleotides to an effector molecule.

Peptides and peptide analogues are very commonly used as effector molecules. In order to attach oligonucleotides by normal nucleotide chemistry to a peptide, the peptide should have free hydroxyl groups. Primary hydroxyl groups are preferred. These can be implemented into a peptide by using protected ethanolamine on the carboxyl end and glycolic acid on the amino terminal, instead of an amino acid. As shown in FIG. 10, serine moieties can be used to give further attachment sites along the peptide backbone.

As shown in FIG. 11, the peptide effector molecule can be branched and used as a multivalent effector structure. Several other multivalent effector structures are possible such as ethylene glycol dimer, trimer, etc. Ethylene glycol derivatives can be connected to polyalcohol to get multivalent effector structures. In order to fully exploit the present invention, conjugation of several nucleic acid chains to a single effector molecule must be possible. The process of combining nucleic acids with polymeric support and with the use of spacer molecules is well known. Similar chemistry can be used in connection with this invention to combine nucleic acid chains with effector molecules such as proteins or polypeptides.

Figure 13:
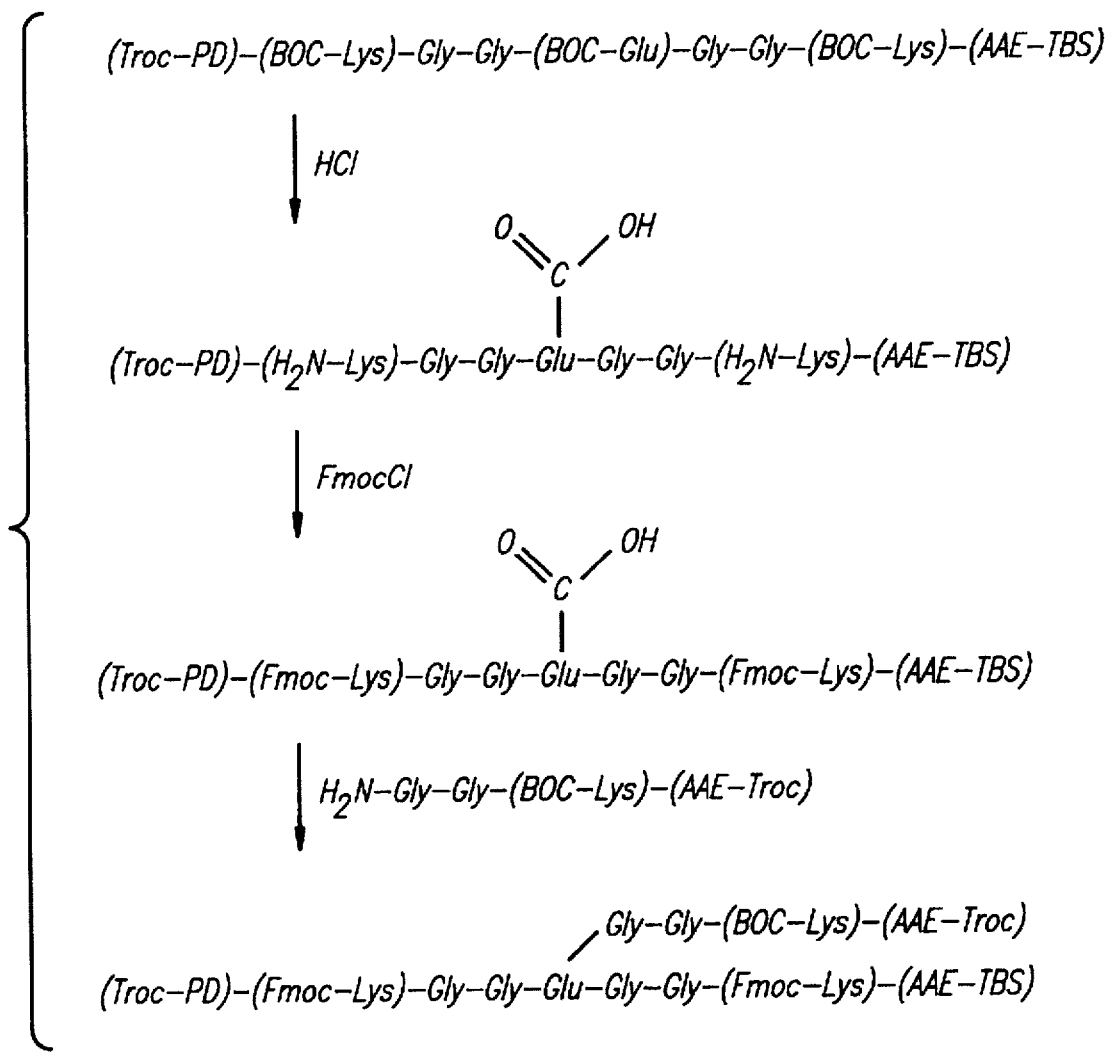
FIG. 13 illustrates an example of the coupling of two derivatized peptide chains to form a branched peptide structure which can serve as a trivalent linker.

One method for conjugating several nucleic acid chains to a single effector molecule is described below. The hydroxyl group of 2-(2'-aminoethoxy) ethanol (AAE) is first protected by t-butyldimethylsilylchloride (TBS). The product is coupled with FMOC-t-BOC-L-lysine. FMOC-group is removed and two FMOC-glycines are attached similarly. FMOC-L-glutaminic acid -t-butyl ester is the next component and will later serve as a branching point (see FIG. 13). Peptide chain is extended with two glycines and one lysine. The amino group of the last lysine is reacted with propylene oxide whereby a secondary hydroxyl group is formed. This hydroxyl group is protected with acid and base stable trichloroethoxycarbonyl group (Troc).

A shorter peptide based chain is synthesized by starting with Troc protected 2-(2'-aminoethoxy)ethanol and coupling this with one lysine and two glycines using standard peptide chemistry.

Two peptide chains which are prepared as described above are coupled together by forming an amide bond between the free carboxylic group of glutaminic acid and the end amino group of the glycine in the shorter peptide. The product which has three branches each having one protected hydroxyl group needs manipulation of the protecting groups before it is compatible with oligonucleotide synthesis.

Figure 14:
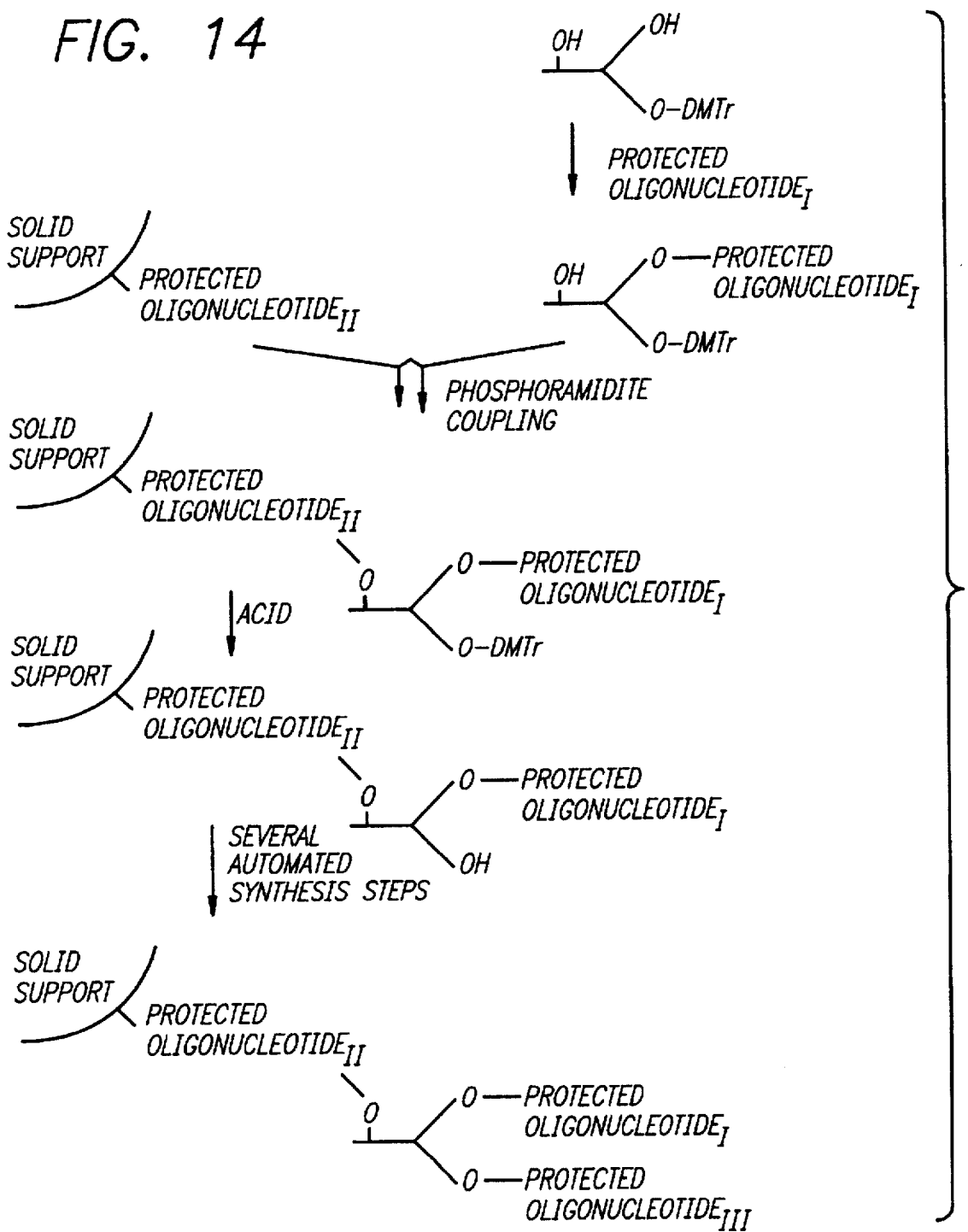
FIG. 14 illustrates an example of a method of using the manipulation of protective groups on a trivalent spacer in order to use the trivalent spacer in oligonucleotide synthesis.

Once the properly protected spacer is prepared, the first prepared oligonucleotide is coupled with phototriester synthesis with the free primary hydroxyl group (FIG. 14). The shortest oligonucleotide is coupled in this stage, whereas the longest oligonucleotide is prepared with automatic synthesizer. The product is not deprotected or detached from the solid support. The synthesis is continued by adding the "trivalent" spacer, which is already coupled with one oligo-nucleotide. The free secondary hydroxyl group becomes coupled with the oligonucleotide which is still bound with the solid support. Thus the peptide spacer is coupled with two oligonucleotide chains. Dimethoxytrityl protecting group of the third hydroxyl group is removed by acid. The automated oligonucleotide synthesis is continued and the third oligonucleotide chain is constructed. The protecting groups are then removed and the molecule is detached from the solid support.

D. Assembly of Supramolecule from Components

The hybridization is performed preferably in a aqueous medium containing various additives. Additives include, but are not limited to buffer, detergent (0.1% to 1%) , salts (e.g., sodium chloride, sodium citrate from 0.01 to 0.2M), polyvinylpyrrolidine, carrier nucleic acid, carrier proteins, etc. Organic solvents may be used in conjunction to water, such as alcohols, dimethyl sulfoxide, dimethyl formamide, formamide, acetonitrile, etc. In addition to concentration of the derivatized oligonucleotides, the temperature can be used to control the hybridization. The optimum temperature for hybridization is 20° C. below the melting point of the oligonucleotide. This means that the preferred temperature for hybridizing 30-mers is typically 40°–60° C. For shorter oligonucleotides the temperature is lower and for longer oligonucleotides it is higher. Oligonucleotides containing large portion of cytidine and guanine have higher melting point than the oligonucleotides containing a lot of adenine and thymidine. Detailed formulae for calculating the melting temperature of double stranded nucleic acids are well known to the person of ordinary skill in the art. Additionally, melting temperature may readily be calculated using empirical methods.

5. Example of Antibody-multienzyme Supramolecule

Two current main strategies for drug development for HIV are finding of reverse transcriptase and HIV protease inhibitors. All four approved AIDS drugs are reverse transcriptase inhibitors. HIV protease inhibitors are also promising as drugs, but the rapid mutation of the viral protease has so far been overwhelming obstacle for the development of a commercial drug.

Embodiments of the supramolecules of the invention that comprise an HIV-antibody and several digestive enzymes can destroy the virus particle itself. Antibodies have earlier been conjugated with enzymes for drug use (C. Bode, M. S. Runge and E. Haber in "The Year in Immunology 1989–1990". Molecules and Cells of Immunity (J. M. Cruse and R. E. Lewis, Eds.) Vol. 6, Karger Publishing, Basel, 1990). Typically these antibody-enzyme complexes are used to produce active drugs from prodrugs. This embodiment of the invention is particularly advantageous if the drug of interest is highly toxic at therapeutic levels. For example, the drug against cancer can be produced on the surface of the cancer cell and cancer cells are subjected to higher concentration of this drug than other cells. Several antibodies specific for cancer cells are known. Enzymes are targeted to degrade the plasma membrane of the cancer cell and include lipases, proteases and glycosidases.

One strategy is to couple lipid and RNA degrading enzymes to an HIV specific antibody. Although a virus does not have its own metabolism to serve as a drug target, a virus is unable to heal itself, if part of the virus is destroyed by externally added catabolic enzymes.

In order for these enzymes to have operational freedom, the spacer between the antibody and the enzyme must be of sufficient, e.g. e.g., on the order of 10 nm. In this case virtually the whole surface of the virus is covered. In order to avoid allergic reactions this spacer must be fully biocompatible, preferably a normal biological component. In addition it should have some rigidity to allow structures in which enzymes and antibodies do not interfere with each other. Because these antibody-enzyme complexes can be complicated structures, a self-assembly would be ideal. Oligonucleotides fulfill all these requirements. Further requirement is that joints connecting enzymes and antibody with oligonucleotides are as small as possible to suppress immunoreaction. These drugs are supramolecular drugs, i.e., noncovalent interactions are important structural factors. Especially complementary hydrogen bonding of oligonucleotides is essential for the assembly and structural integrity.

Figure 3A:
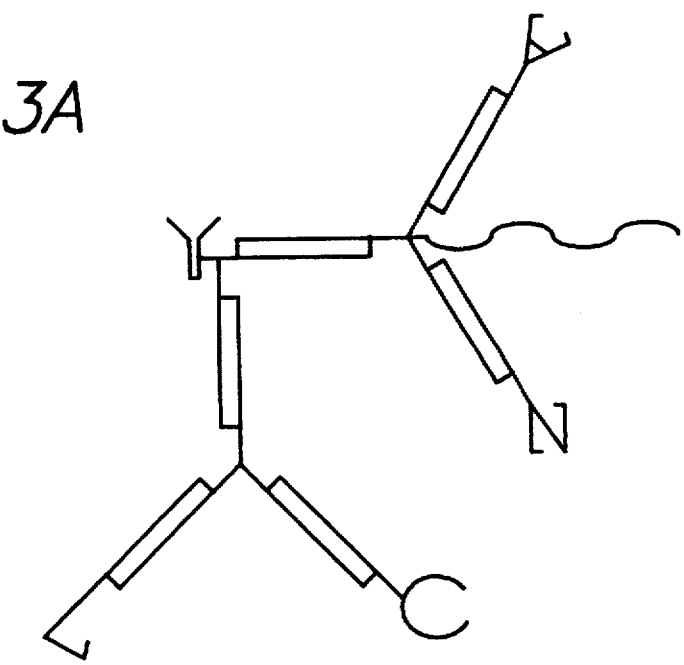
FIG. 3(A) is a schematic representation of the construction of an antibody-multienzyme supramolecule constructed from supramolecular subcomponents.
Figure 3A:
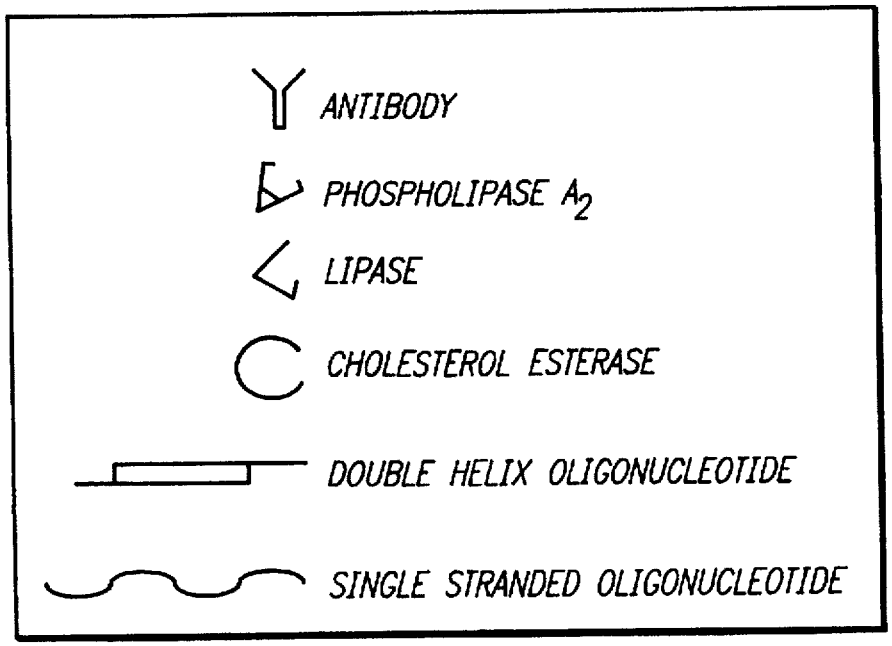

In FIG. 3A is a schematic representation of one possible supramolecule demonstrating this principle. Antibody is in central position and four different enzymes: phospholipase $A_2$, lipase, cholesterol esterase and ribonuclease A. Phospholipase $A_2$ can be supplemented or completely replaced by another phospholipase such as phospholipase C. One extra single stranded oligonucleotide is attached with the antibody. This oligonucleotide is complementary with viral RNA and binds viral RNA when virus is disintegrated.

Many viruses, including HIV-1, are covered by a lipid bilayer which it takes from the host cell when it is formed. The bilayer contains phospholipids, triglycerides and cholesterol esters. Accordingly three enzymes specific for these classes of compounds are used to digest the viral lipid bilayer. When the bilayer is hydrolyzed, fatty acids and lysolipids are formed. These digestion products are soluble in blood plasma and may be bound by albumin, which is a scavenger protein to remove free fatty acids and lysolipids. When the protein core of the virus is exposed to plasma it is to be expected that the protein dissolves spontaneously and RNA is released. This process happens when the virus is internalized into a cell. The lipid bilayer fuses with the plasma membrane of the cell and virus becomes unstable and dissolves into the cytoplasm of the cell. No specific endocytosis mechanism has been observed for HIV. In essence our idea is to induce the dissolution of the virus outside the cell and destroy viral RNA when it is released. In order to promote the breakdown of RNA a short complementary oligonucleotide is attached with the antibody and also ribonuclease A is part of the enzyme palette. Proteinases are not included among the enzymes in our first design, because it is feasible to suppose that the protein effector of the HIV is unstable when exposed. If opposite turns out to be true, it is possible to include some proteinases. However, blood contains inhibitors against many proteinases, especially if proteinases are nonspecific. Some specific endopeptidases as well as carboxypeptidases and aminopeptidases can be used, because they are not inhibited.

A similar strategy can be used for cancer therapy and to remove 'plaque' from blood vessels, e.g., to treat atherosclerosis. In each case antibody must be replaced with another antibody or other recognition molecule, which is specific for the target. Also enzymatic composition must be adjusted for each application.

Figure 3B:
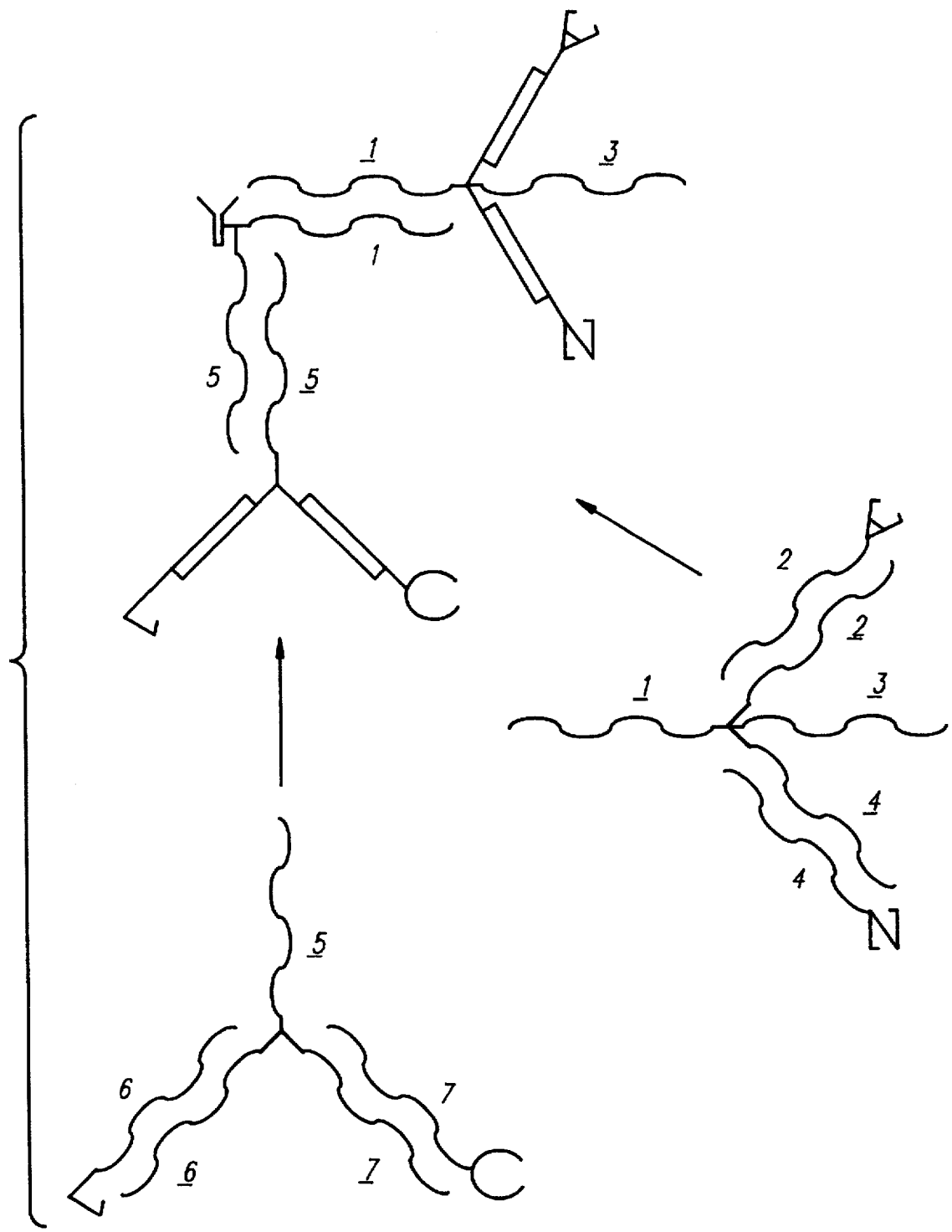
FIG. 3(B) is a schematic representation of the construction of supramolecular subcomponents used in FIG. 3(A) from molecules each containing one enzyme or antibody.
Figure 3C:
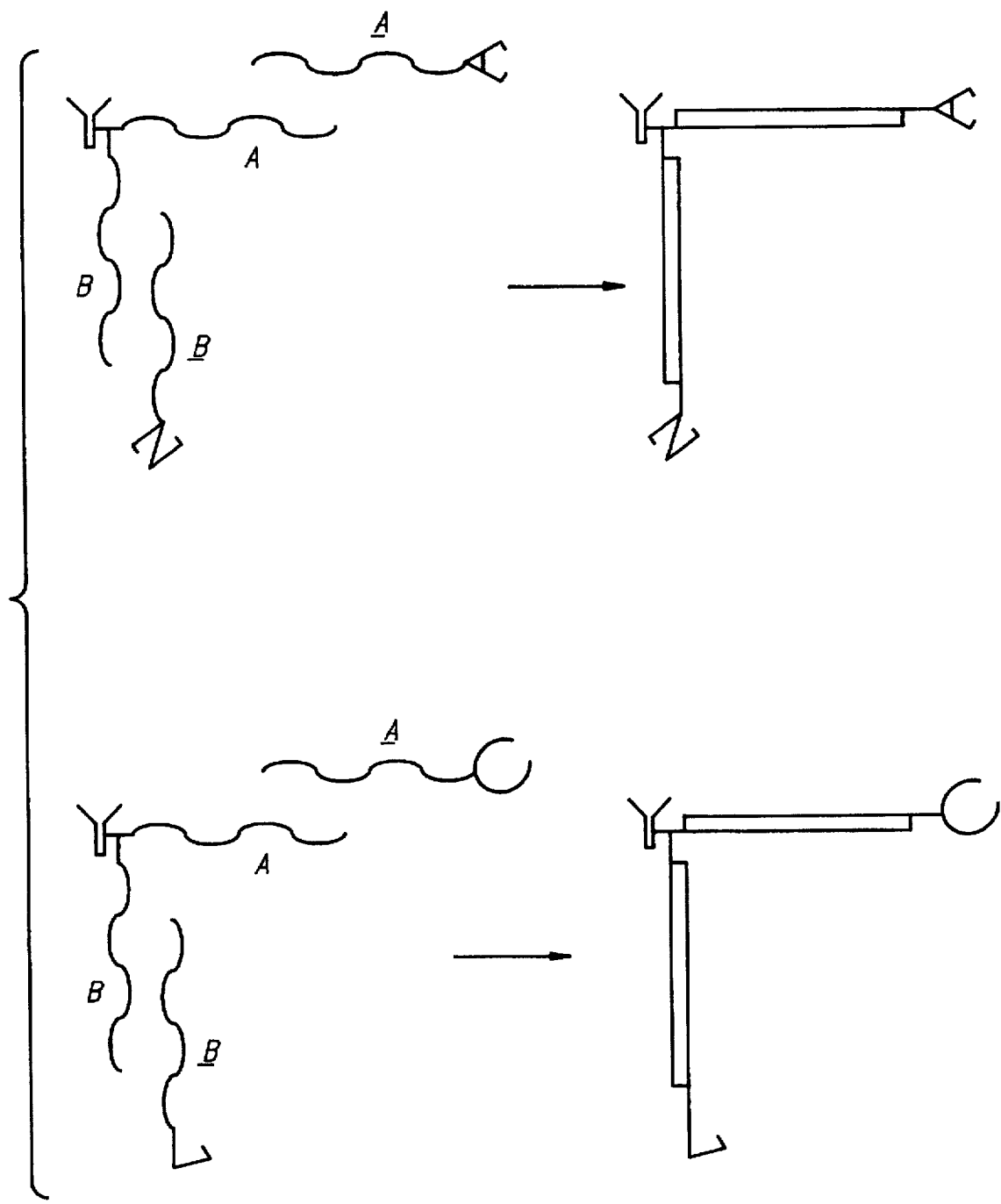
FIG. 3(C) is a schematic representation of the construction of two supramolecules containing an antibody and two enzymes. The combination of these two supramolecules is able to degrade all lipid components of the virus.

The antibody-multienzyme supramolecule is assembled from oligonucleotide-enzyme conjugates and branched oligonucleotides according to FIG. 3(B). FIG. 3(C) depicts two simplified supramolecules, which together can carry the same enzymes as the supramolecule in FIG. 3(A).

An important consideration in the synthesis is the incorporation of amino or thiol functionalities into a desired point of the oligonucleotide during automated synthesis. Phosphoramidite synthesis is described in 5.1–5.7. Their use in oligonucleotide synthesis is straightforward. By using amino and thiol specific cross-linking agents, the synthesis of branched oligonucleotides is also easily accomplished. The oligonucleotide strands are by A and B and their complementary oligonucleotides are denoted by corresponding underlined letters. Enzymes are attached into either 3' or 5'-terminus of the oligonucleotide, which contains an amino group. This kind of coupling of oligonucleotides and proteins is a standard practice in biochemical conjugation. Antibody is attached into the center of a oligonucleotide chain containing an aliphatic amino group in that position.

After molecular building blocks are synthesized, the final step is a self-assembly of a supramolecule. This relays on the pairwise complementarily of the oligonucleotide strands in the components, which are designed to bind together. In principle, the components contain the complete information of the structure of the final supramolecule and a simple mixing of the component molecules will produce the wanted product. However, in order to make certain that the assembly proceeds as designed, the stepwise process is to be preferred. Preparation of the antibody-multienzyme supramolecule Abbreviations: Aminopropanol, AP; 2-Cyanoethyl N,N-diisopropylchloro phosphoramidite, CEDIPCPA; Dichloromethane, DCM; Di-isopropyl ethyl amine, DIPEA; Fluorenylmethoxycarbonyl, FMOC; Fluorenylmethoxycarbonylchloride, FMOCCl; Methanol, MeOH; Monomethoxytrityl, MMT; Monomethoxytritylchloride, MMTCl; Serinol, SER; Tetrahydrofurane, THF; Triethylamine, TEA.

5.1. N-Monomethoxytrityl Aminopropanol (MMT-AP)

MMTCl (1.54 g) in 10 ml of DCM was added to a solution of AP (1.5 ml) in 5 ml of DCM. The reaction mixture was 24 h at +4° C. 10 ml of DCM was added and the mixture was washed twice with 10 ml of 5% $NaHCO_3$ and with 5 ml of water. The DCM phase was dried with solid $NaHCO_3$. The solution was concentrated into 5 ml in vacuo and applied to 40 g silica column, which was eluted with 300 ml of DCM/TEA 200:1, 300 ml of DCM/EtOAc/TEA 200:2:1 and 200 ml of DCM/EtOAc/TEA 100:2:1. 1.32 g of pure MMT-AP was obtained.

5.2. N-Monomethoxytrityl aminopropyl cyanoethyl N,N-diisopropylphosphoramidite (MMT-AP-CEDIPPA)

To a solution of MMT-AP (0.42 g) in 8 ml of DCM was added 475 µl of EDIPA and 0.30 g Of CEDIPCPA in 2.5 ml of DCM. After 10 min the reaction mixture was applied directly to 10 g silica column. The column was eluted with DCM/EtOAc/EDIPA 98:1:1. Fractions of 6 ml were collected. The product was in fractions 3 and 4. The yield was 0.44 g.

This product was used in oligonucleotide synthesis.

5.3. N-Fluorenylmethoxycarbonyl aminopropanol (FMOC-AP)

FMOCCl (1.55 g) in 10 ml of THF was added into a solution of 0.90 g of AP in 40 ml of water. After 30 min stirring the reaction mixture was extracted with 20 ml of DCM. The DCM solution was washed twice with 10 ml of water and dried with $MgSO_4$. The solvent was removed with a rotary evaporator and the residue was dissolved into 14 ml of EtOH and 14 ml of water was added. The small precipitate was filtered off and the solution was put into a refrigerator. After 20 h the precipitate was separated by filtration. The yield was 1.22 g.

5.4. N-Fluorenylmethoxycarbonyl aminopropyl cyanoethyl N,N-diisopropylphosphor-amidite (FMOC-AP-CEDIPPA)

FMOC derivative was done exactly as MMT analog in Example 2 using 0.30 g FMOC-AP. Also purification was done similarly. The product was in fractions 3–8. Fractions 3–7 contained 0.41 g product.

This product was used in oligonucleotide synthesis.

5.5. N-Fluorenylmethoxycarbonyl Serinol (FMOC-SER)

FMOCCl (1.55 g) in 10 ml of THF was added into a solution of 0.54 g of SER in 30 ml of water and 8 ml of 1.5-M $Na_2CO_3$. After 30 min stirring the reaction mixture was extracted with 20 ml of EtOAc. The EtOAc solution was washed twice with 10 ml of water and dried with $MgSO_4$. The solvent was removed with a rotary evaporator and the residue was dissolved into a mixture of 5 ml of EtOH and 30 ml of DCM. The product crystallized in +4° C. Yield was 1.12 g.

5.6. N-Fluorenylmethoxycarbonyl O-dimethoxytriphenyl serinol (FMOC-DMT-SER)

FMOC-SER (1.12 g) was dissolved into 6 ml of pyridine and 0.68 g of solid DMTrCl was added. The reaction mixture was put into +4° C. After 20 h 20 ml of water was added and the oily layer was washed with 5 ml of water and dissolved into 10 ml of EtOAc and the solvent was removed in vacuo. The residue (1.76 g) was fractionated in 28 g silica column, which was eluted with DCM/EtOAc/MeOH/TIPEA 98:1;0.2:0.5 and 96:4:1:0.5. Yield of pure product was 0.72 g.

5.7. N-Fluorenylmethoxycarbonyl O-dimethoxytriphenyl serinyl cyanoethyl N,N-diisopropylphosphoramidite (FMOC-DMT-SER) CEDIPPA)

FMOC-DMT-SER derivative was produced essentially as described for the phosphoramidite in Example 5.2 using 0.65 g FMOC-AP. The product was purified similarly. The desired reaction product was found in fractions 4–9. Fractions 5–8 contained 0.82 g product. TFMOC-DMT-SER may also be synthesized by first protecting serinol with DMT and then with FMOC. This variation allows also acylation of the amino group of serinol with carboxylic acid carrying various other functionalities, such as protected amino or thiol groups and biotin.

The desired product was used in automated synthesis to introduce aliphatic amino group in the position of 20 in a 51-mer.

5.8. Automated Synthesis of Oligonucleotides

The following oligonucleotides were synthesized by automated synthesis:

A 3'TGGAGATGGGGCACCATGCTX5' (SEQ ID NO:1)

B 3'AGCATGGTGCCCCATCTCCAYAGTCA-CAGCACAGCACTAATAACAAGAAA5' (SEQ ID NO:2)

C 3'TYTTTCTTGTTATTAGTGCTGTGCTGTGACT5' (SEQ ID NO:3)

D 3'GTGATAGGAGTTGATTACAGTCCTX5' (SEQ ID NO:4)

E 3'AGGACTGTAATCAACTCCTATCACYAT-CAGAAGAGTGAGACGGTGGGAT5' (SEQ ID NO:5)

F 3'TYATCCCACCGTCTCACTCTTCTGAT5' (SEQ ID NO:6)

G 3'TAGACTCAGCGCAATCGTGAAGCTX5' (SEQ ID NO:7)

H 3'AGCTTCACGATTGCGCTGAGTCTAYGAT-TCTCGGCTCGTTCGAAGTGTC5' (SEQ ID NO:8)

I 3'TYGACACTTCGAACGAGCCGAGAATC5' (SEQ ID NO:9)

X represents MMT-AP-CEDIPPA (5.2) and Y represents FMOC-DMT-SER-CEDIPPA (5.7). Analogous amidires may also be to introduce aliphatic amino groups.

5.9. Purification of Monoclonal Antibody

Anti gp41/160 ( antibody IAM3D6) supernatant had a concentration of 315 mg/l. It was purified in 160 ml portions in Protein A Sepharose Fast Flow 5 ml column. The supernatant was buffered with 40 ml of 0.2-M $Na_2HPO_4$. After feeding the supernatant into the column, the column was washed with 120 ml of 0.1-M $Na_2HPO_4$. The antibody was eluted off the column with 0.1-M citric acid and neutralized immediately with 3-M KOH. The antibody solutions were stored at −18° C.

5.10. Acetylated Protein A Sepharose Gel

Protein A Sepharose was packed into 1.5 ml column. It was saturated by eluting with a solution containing 50 mg of monoclonal antibody (Anti gp41/160 IAM3D6). The column was washed with 0.1-M $Na_2HPO_4$ buffer (15 ml) and eluted 10 ml 1 mM acetyl N-hydroxy succinimide solution in DMF/water 1:9. The antibody was removed by 0.1-M citric acid. The acetylated Protein A Sepharose was used to couple antibody with nucleotides and in the final assembly of the supramolecule.

5.11. Coupling of Oligonucleotide with Antibody

A solution of antibody (40 mg /25 ml water) was eluted through the column containing 1.5 ml acetylated Protein A Sepharose. The Sepharose was washed with 3 ml of 0.1-M $Na_2HPO_4$ and taken out of the column to perform a bath reaction with derivatized nucleotide.

Oligonucleotide 2 (10 mg, 0.5 μmole), comprising two equal 30-mers bound together by an amino group containing joint, was dissolved into 1 ml of 0.1-M $NaHCO_3$ and 50 μl of 1-M solution of bis(hydroxysuccinimidyl) glutarate in acetonitrile was added. After one hour the water solution was extracted twice with 1 ml of EtOAc and the solution was dialyzed 2 h against 0.1-M $NaHCO_3$. The activated nucleotide was added into a slurry of Sepharose. The mixture was stirred six hours and packed into a column. The antibody coupled to the nucleotide was eluted off the column with 0.1-M citric acid. Antibody-oligonucleotide conjugate was fractionated in a Sephadex G-25 column and antibody connected with oligonucleotide was collected.

5.12. Coupling of Oligonucleotide with Enzymes

Oligonucleotide 1 (20 mg,2 μmole), which was contained aliphatic amino group at 5'-position was dissolved into 2 ml of 0.1-M $NaHCO_3$ and 400 μl of 1-M solution of bis (hydroxysuccinimidyl) glutarate in acetonitrile was added. After one hour the water solution was extracted twice with 1 ml of EtOAc. The solution was dialyzed 2 h against 0.1-M $NaHCO_3$ and 0.5 ml aliquots of this solution were added into the following enzyme solutions:

a. 10 mg phospholipase $A_2$ in 1 ml of water.

b. 40 mg lipase in 4 ml of water.

c. 10 mg ribonuclease in 1 ml of water d. 30 mg carboxypeptidase in 3 ml of water

5.13. Assembly of the Supramolecule

Antibody connected with oligonucleotide was eluted through a acetylated Protein A Sepharose column (1.5 ml) so that the column was saturated with antibody. The column was thermostable at +40° C. and phospholipase-oligonucleotide conjugate solution (twice the equivalent amount) was circulated through the column and UV-flow cuvette. When UV-absorption at 280 nm was decreased into half the ribonuclease A-oligonucleotide conjugate was circulated similarly through the column. Generally about two hours was needed for a complete reaction. The supramolecule was eluted off the column by 0.1-M citric acid and neutralized immediately with 1-M KOH. The other supramolecule depicted in FIG. 3(C) was prepared similarly.

6. Design of Supramolecule for Capturing Virus Particles

This example describes the design of a supramolecular assembly that is capable of surrounding a comparatively large particle, e.g, a virus. First, a structure, which is capable of performing the desired function, is designed and the geometrical features are fixed. Then chemical and physical features are chosen based on the application. Hydrophilicity, hydrophobicity, acidity, alkalinity, charge transfer, etc., is mapped onto the structure. This designed structure may be visualized as a single molecule, although in many instances the synthesis of this molecule would be difficult to achieve at a reasonable yield. In such embodiments, supramolecular retrosynthesis is performed, i.e., the structure is broken down into small molecules, which are capable via self-assembly of forming the original structure. The supramolecular assembly produced in this manner is not identical with the molecule represented as a schematic in the figures; however, the important characteristics, i.e., geometry and chemical and physical properties listed above, remain the same. Supramolecular retrosynthesis does not try to retain the original molecular structure intact, but tries to retain all the important chemical and physical properties of the desired structure.

Another retrosynthetic cycle can be performed for the molecules obtained in the previous retrosynthesis to obtain smaller molecular building blocks. Finally, molecules are obtained that can be designed and prepared easily. In the design example given below, there are two retrosynthetic cycles.

Figure 4:
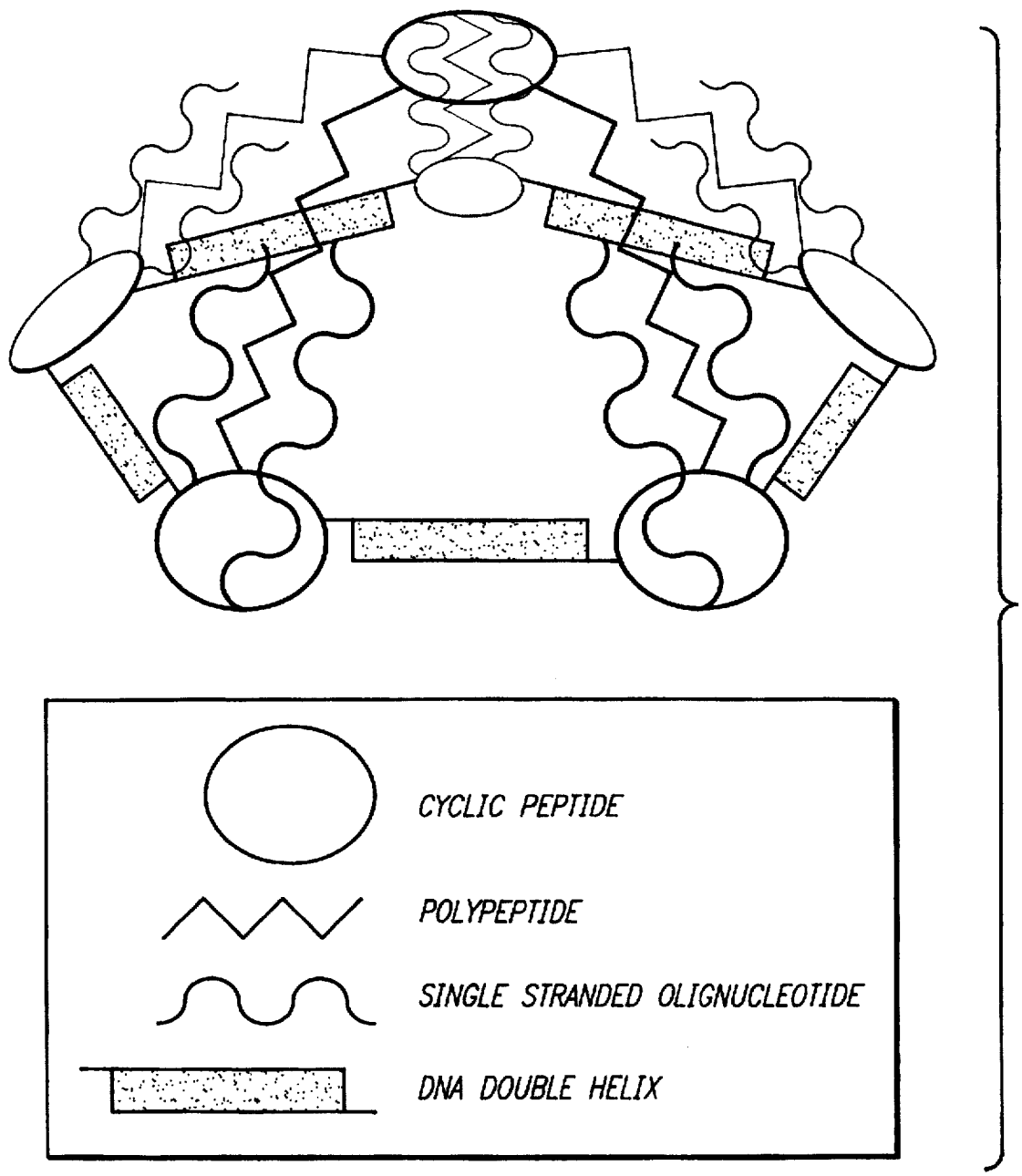
FIG. 4 is a schematic representation of a supramolecule subcomponent which is capable of forming a supramolecular cage around a virus when it combines with a complementary supramolecule subcomponent.
Figure 5A:
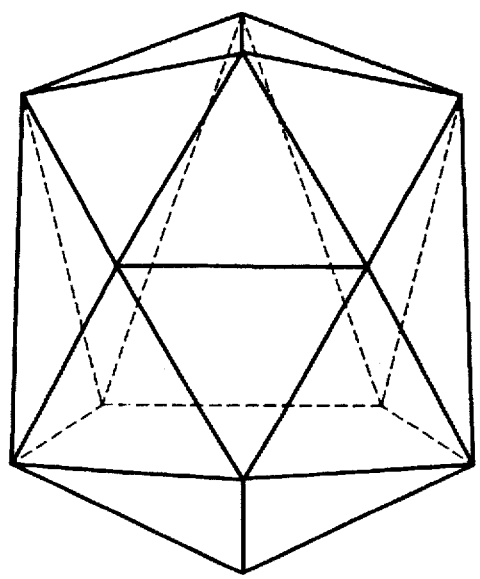
FIG. 5A is a schematic representation of a typical icosahedral virus.
Figure 5B:
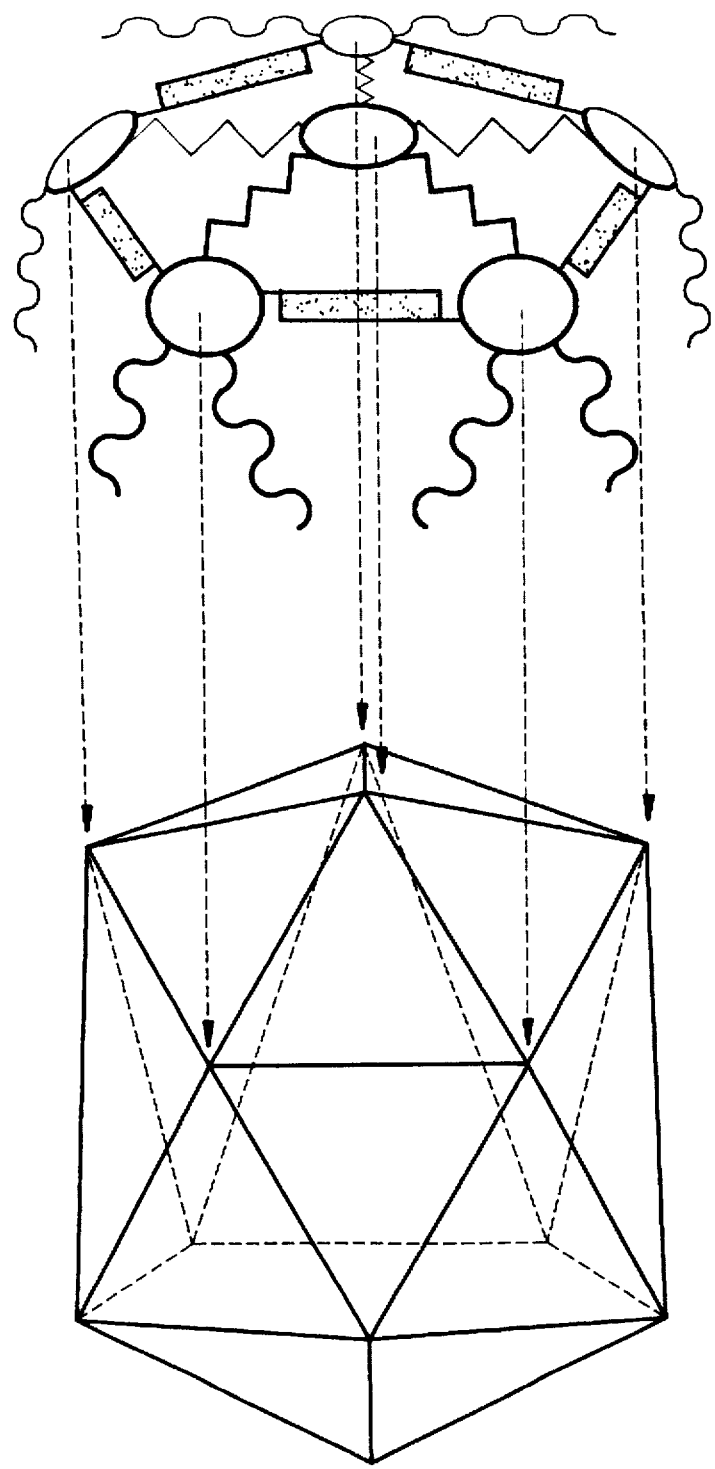
FIG. 5B is a schematic representation of the supramolecule subcomponent of FIG. 4 approaching the icosahedral virus.
Figure 5C:
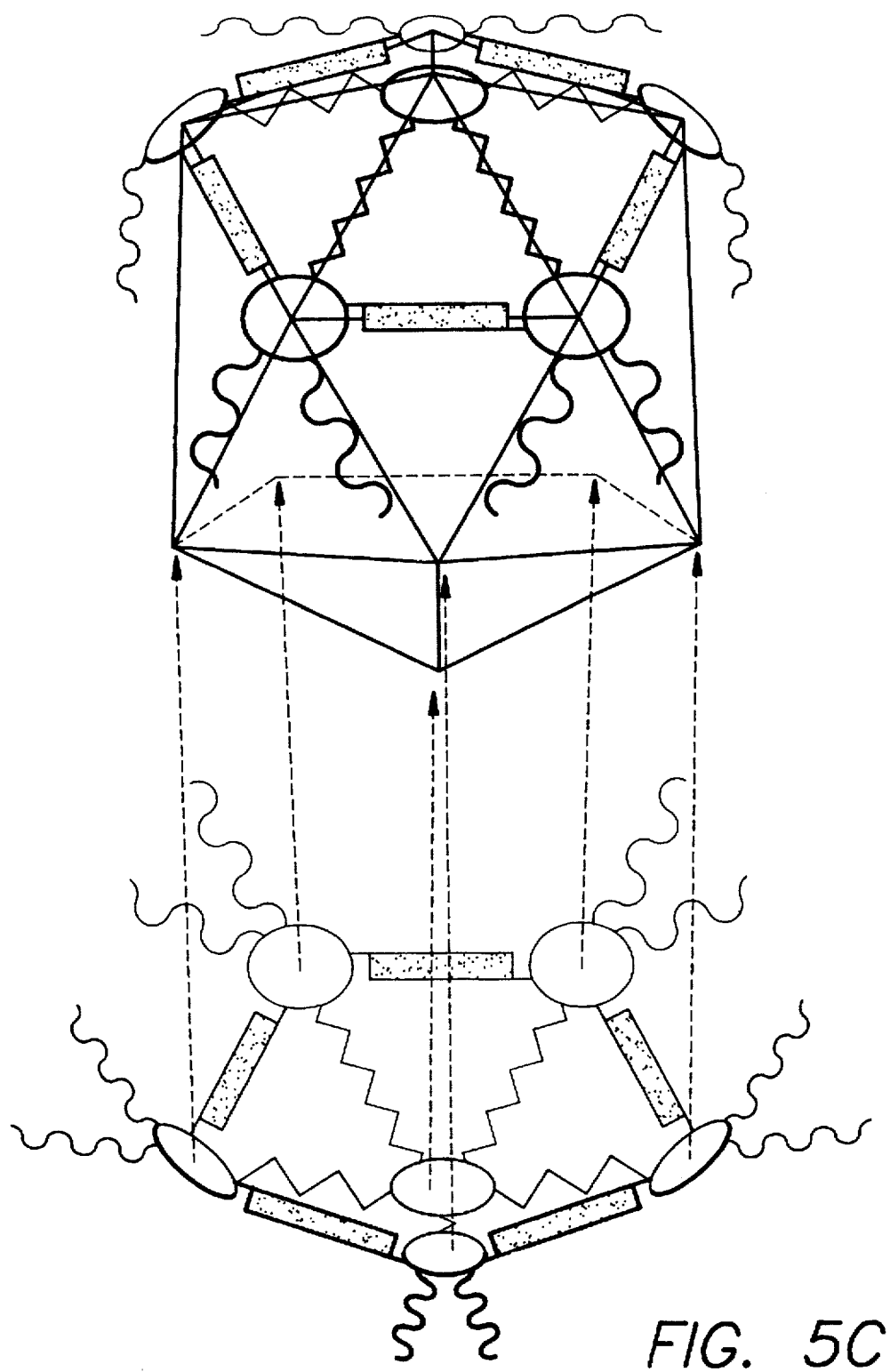
FIG. 5C depicts a second, complementary supramolecule subcomponent approaching the icosahedral virus.
Figure 5D:
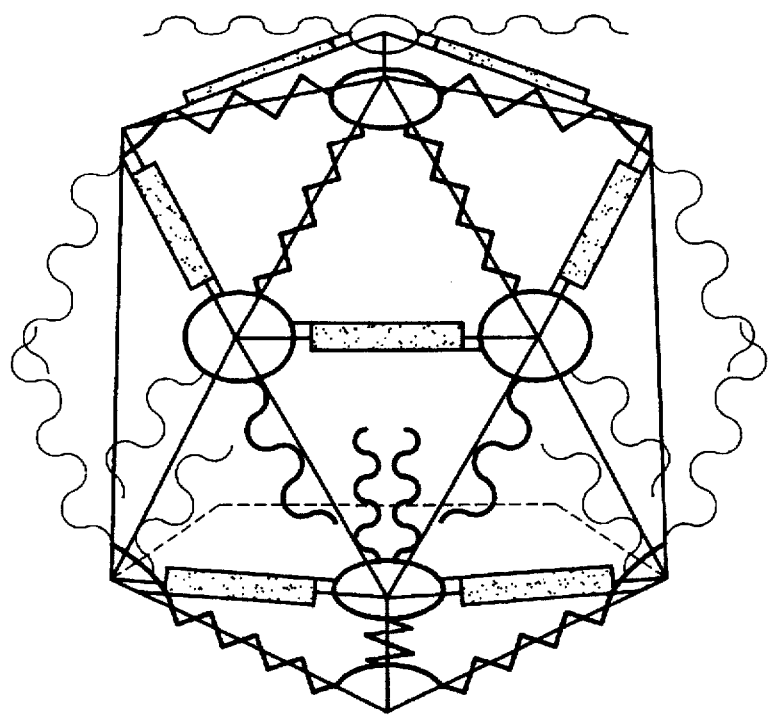
FIG. 5D depicts two complementary supramolecule subcomponents surrounding a icosahedral virus.
Figure 5E:
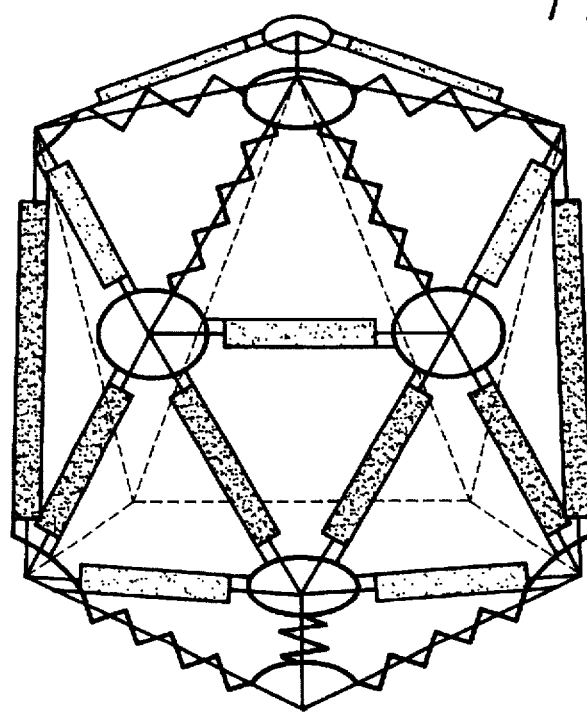
FIG. 5E depicts a icosahedral virus encased within a supramolecule.

Many viruses have an icosahedral shape. Such a virus can be covered by an icosahedral and assembly designed according to this invention. This process is demonstrated stepwise in FIGS. 5 A–E. Dimensions referenced are taken from HIV (human immunodeficiency virus), but the same principles apply to any virus. In this example, polypeptides and oligonucleotides are used, because synthetic methods are available for their high yield synthesis. As synthetic methods further develop, analogues or completely artificial supermolecular systems can be made using the same design and construction principles offered by the invention.

Each edge of HIV is about 80 nm. In preliminary design we suppose that three amino acid or nucleic acid residues are needed per nanometer. The circles in FIG. 4 represent cyclic polypeptides containing enough lysine so that five polylysine chains can be attached. These polylysines are denoted by zig-zag lines in FIG. 4. Polylysine should contain about 200 residues in order to cover whole edge. Onto the other end of each polylysine chain is coupled another cyclic peptide that has four nucleotides attached. These nucleotide strands are denoted by a wavy line in FIG. 4. Two of these oligonucleotides are the same, for example, oligonucleotide 1 (n=p=1, i=100). Two others are mutually complementary, but they are bound to the cyclic peptide so that coupling occurs easily between neighbors, but not intramolecularly. Thus, they form a pentagon shaped double helix. FIG. 4 shows single stranded oligonucleotide is bound by polylysine. Another molecule is designed using the same principles, but instead of oligonucleotide 1, the single stranded oligonucleotide is now 1. When either of these molecules encounters a virus, which has a negatively charged surface, polylysine is Coulombically associated with the virus. Simultaneously, a negatively charged oligonucleotide (e.g., 1 or $\underline{1}$) is released from the polylysine. When a complementary capping molecule is associated with the virus, the complementary oligonucleotides ($\underline{1}$ and 1) combine to close the cage from which the virus can not escape.

The molecules shown in FIGS. 4–5 and described above would be incredibly difficult to synthesize. However, by designing a supramolecular constructed from smaller components, synthesis of a virus capturing molecule is made possible.

FIG. 6 demonstrates how the analogous structure for the large molecule in FIG. 4 can be prepared using smaller molecules. These smaller molecules are shown separately in FIG. 6. Thus, in this approach six different compounds are needed to get the overall structure, which is same as that of the molecule in FIG. 4. Four of these are relatively simple, because in each two oligonucleotides are connected to a spacer, which can be polypeptide. Two molecules in the upper part of FIG. 4 are still relatively complicated because in both cases five nucleotides are connected to a cyclic spacer, which can be a cyclic peptide. These oligonucleotides are denoted by (3,3,3,3,3) and (1,1,8,$\underline{7}$,8). In these notations only free single stranded oligonucleotides are listed. These structures can be synthesized by attaching each type of oligonucleotide needed to a short peptide, for example, pentapeptide Gly-Ala-Ser-Ala-Gly which is otherwise protected but the hydroxyl group of serine is free. Nucleotide is connected with this hydroxyl group using normal phosphate coupling. Then, using peptide synthesis methods, these pentapeptides connected to a specific oligonucleotides are coupled in a desired order. Closing the cycle makes the molecule more symmetric, but is not essential for the supramolecular assembly or the function of this assembly in most cases.

There is a further possibility of assembly of cyclic structures containing five oligonucleotide chains by using the general principles of this application. This second step of supramolecular retrosynthesis is demonstrated in FIG. 8. Both of these cyclic structures can be assembled from five smaller molecules. For (3,3,3,3,3) these molecules are twice (3,1,$\underline{2}$) and once (3,2,$\underline{4}$), (3,2,4), (3,1,2) and for (1,1,8,$\underline{7}$,8) these are ($\underline{2}$,1,6), ($\underline{6}$,1,$\underline{5}$), (5,8,$\underline{4}$), (4,$\underline{7}$,3), (3,8,2). In these notations it is immediately clear that molecule ($\underline{2}$,1,6) combines with the molecule ($\underline{6}$,1,$\underline{5}$), because complementary nucleotides are written last and first, respectively. Looking at the whole sequence of five molecules indicates that the notation starts with nucleotide $\underline{2}$ and ends with 2. This means that these ends will bind together and form a pentagon. After assembly, a supramolecule is obtained which has the same overall shape as two molecules in upper part of FIG. 7.

These supramolecules are still denoted by listing only their single stranded oligonucleotides, because this is important for further assembly and is sufficient for purposes of this application. The symbols are (3,3,3,3,3) and (1,1,8,7,8). These supramolecules also function similarly in further assembly of the structure, which has the same shape as the molecule in FIG. 4. This demonstrates that almost any structure can ultimately be created from molecules which has a spacer or a molecular moiety having an active role in the final assembly connected to two or three oligonucleotides. The spacer can be a very small molecule or it can be a large molecule. The spacer can actually be a DNA strand.

Figure 8:
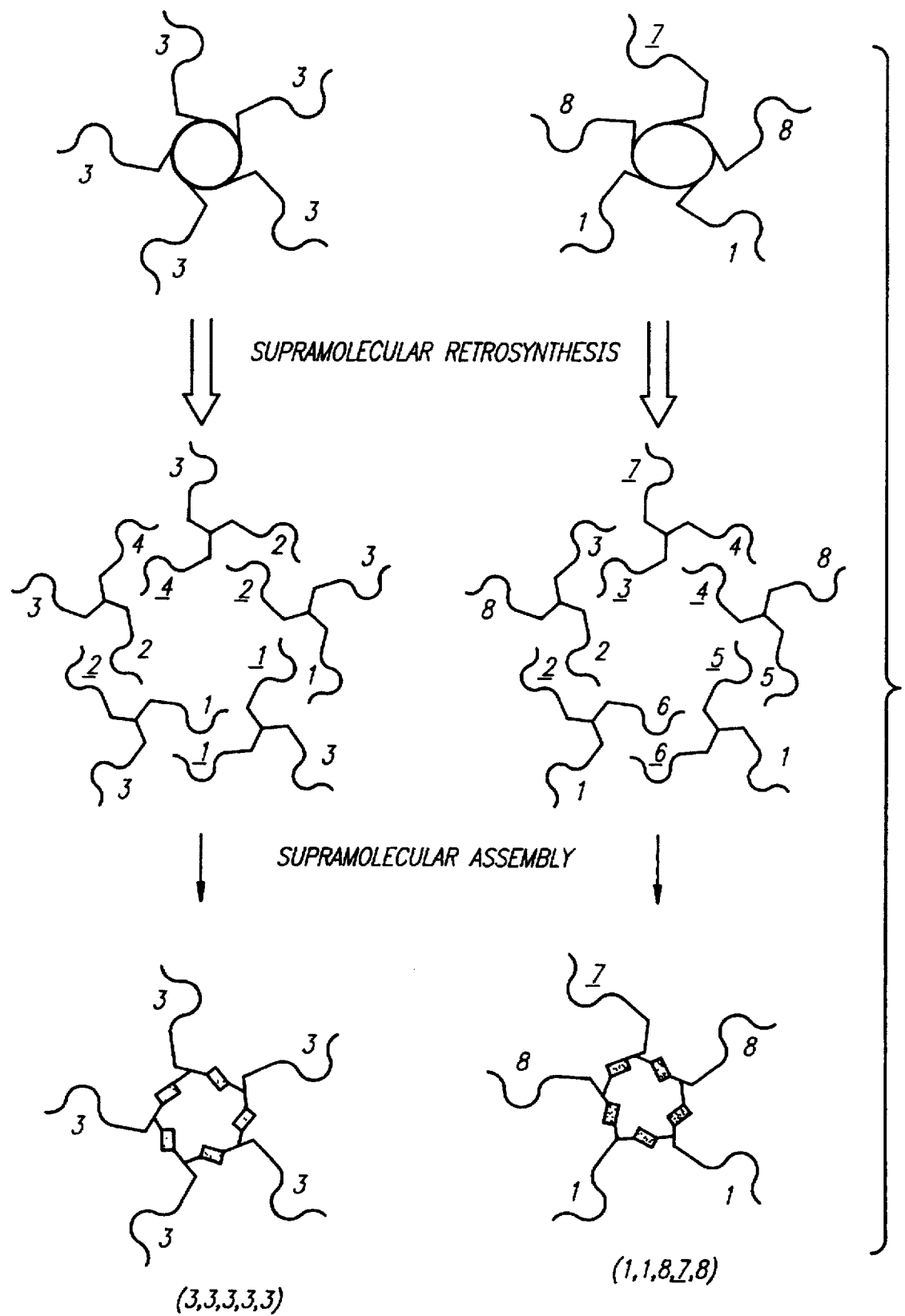
FIG. 8 is a schematic representation of supramolecular assemblies which are similar to the molecules shown in FIG. 6.
Figure 9:
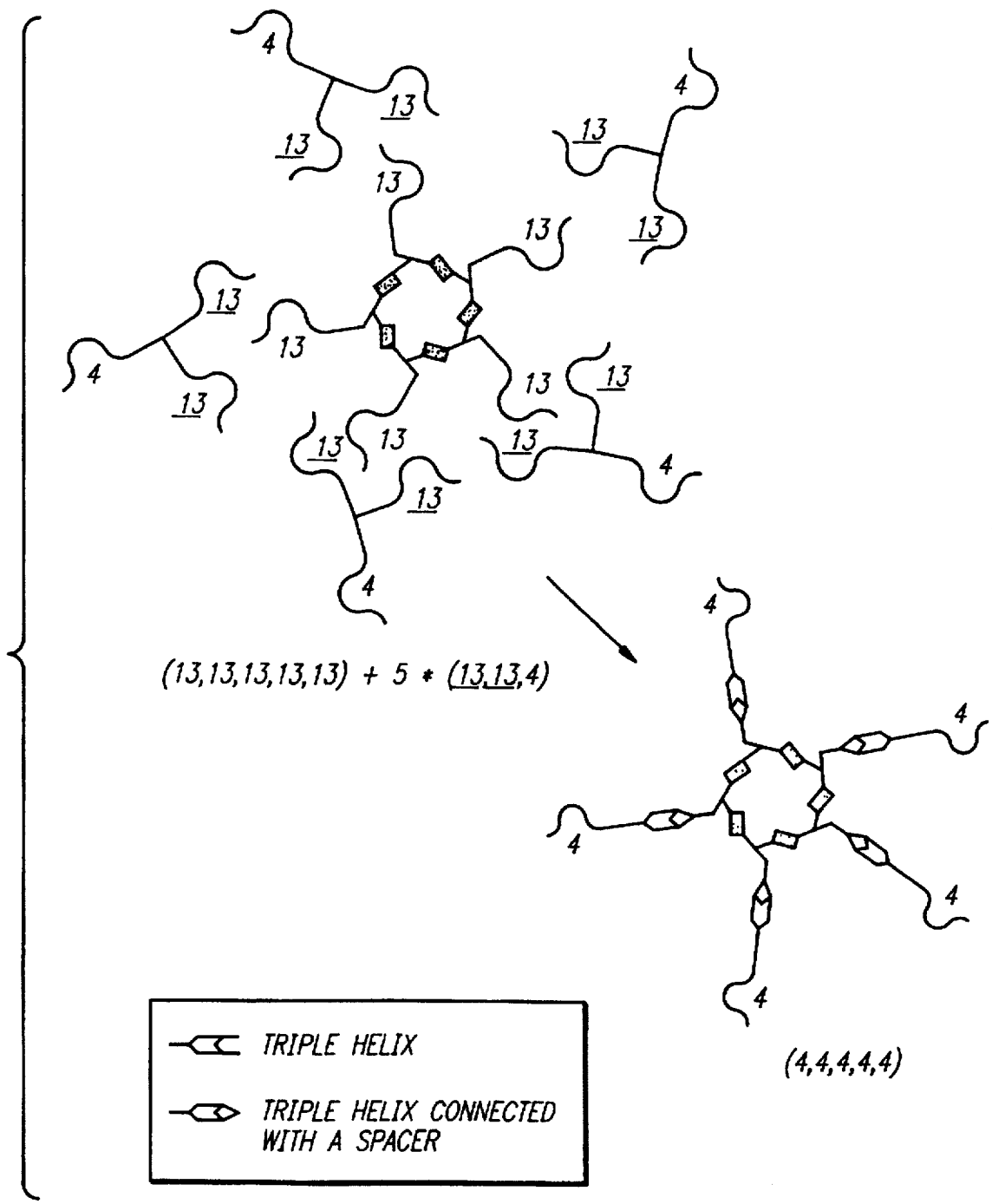
FIG. 9 is a schematic representation of the use of triple helices in supramolecular assemblies.

Supramolecular assemblies are preferably prepared in an aqueous environment, although some embodiments may be assembled in organic solvents. When effector molecules are lipophilic, the Langmuir-Blodgett technique may be utilized. Stepwise assembly is often advantageous. For example, the cyclic structures (3,3,3,3,3) and (1,1,8,7,8) in FIG. 8 are assembled separately. These two structures can be stabilized internally by cross-linking their double helices. This cross-linking can be performed in a highly selective manner. By cross-linking, both of these supramolecular assemblies become covalent molecules. Cross-linking is not essential, but can be advantageous, because it increases thermal stability. After first assembly and possible cross-linking, the product can be purified. Purification as well as cross-linking is to be recommended, if the same oligonucleotide is used in several different places.

Figure 6:
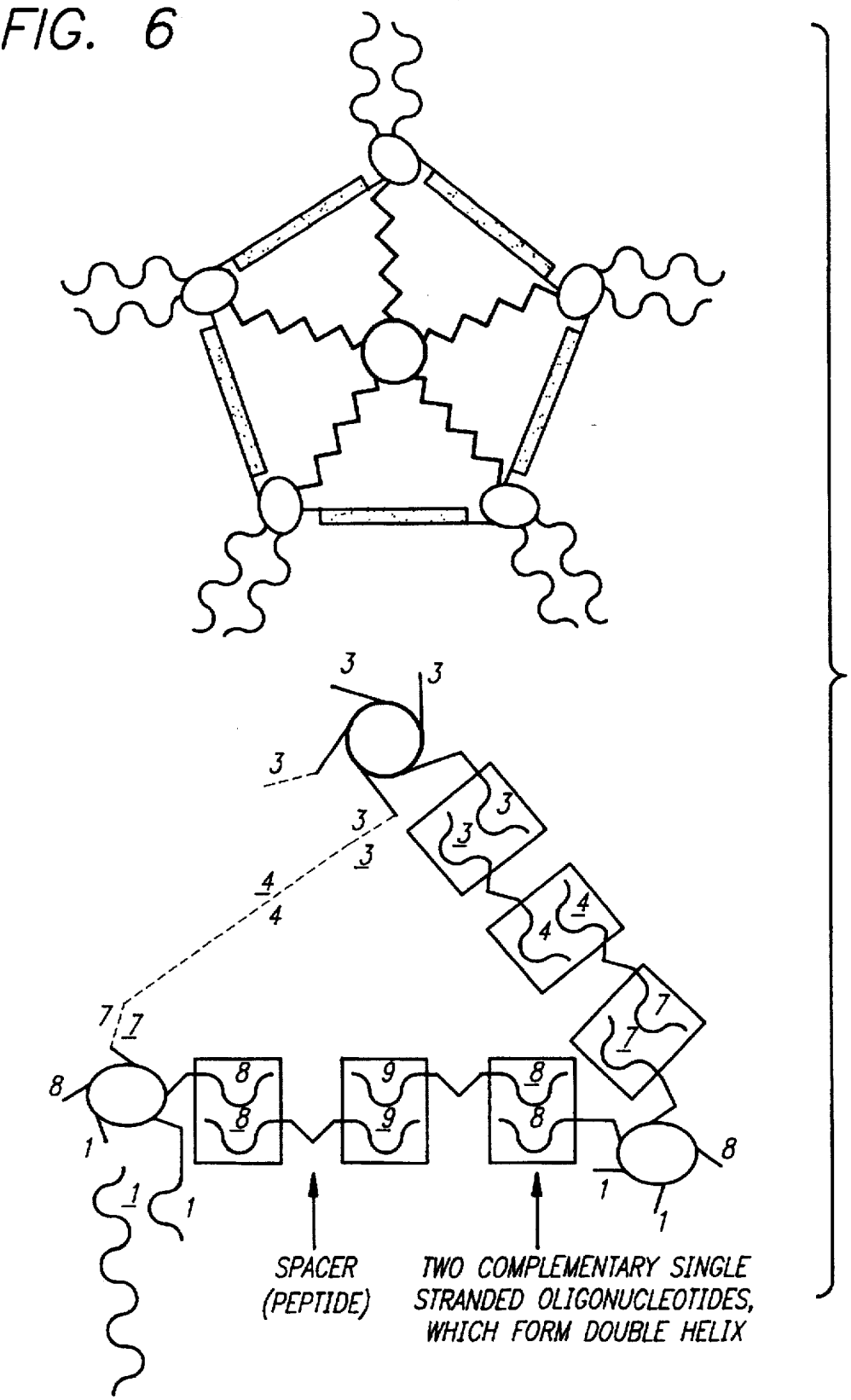
FIG. 6 is a schematic representation of how the analogous structure for the large molecule in FIG. 4 can be prepared using smaller molecules.
Figure 7:
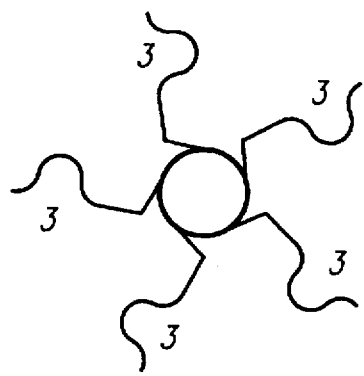
FIG. 7 is a schematic representation of molecules needed to construct the supramolecule of FIG. 5.
Figure 7:
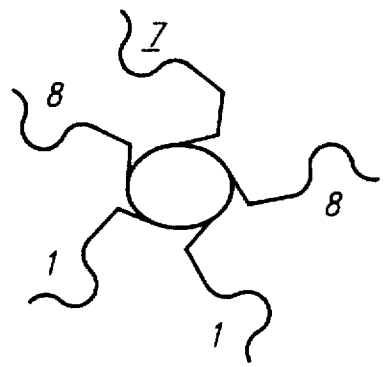
Figure 7:
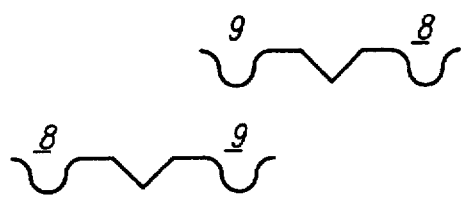
Figure 7:
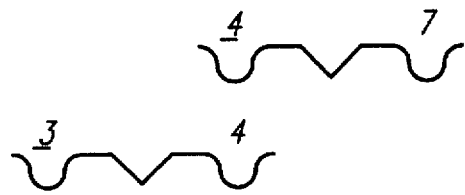

During the second assembly step (3,4) and (4,7) (see FIG. 6) are added to (3,3,3,3,3) to give (7,7,7,7,7). In the third assembly step the product (7,7,7,7,7) and (1,1,8,7,8) are combined to form 10*(1,8). The fourth assembly step is the formation of a pentagon by adding (8,9) and (8,9) to give 10*(1). The fifth and final assembly step is adding single stranded oligonucleotide 1, and the end product is 10*(1). After each step, cross-linking or purification or both can be performed depending on the final requirements regarding quality of the product. The complementary supramolecule 10,(1) is prepared similarly.

If necessary, the cage surrounding the virus can be made more dense using the principles of this application. The number of molecules needed is then correspondingly larger.

DNA double helix is thermally unstable and cross-linking may be required for stability. One possible approach is shown in FIG. 12. The last amino acid residue in the spacer is lysine and a complementary DNA strand contains an alkylating group, which binds preferentially with the amino group of lysine, because it is the most nucleophilic of the functional groups in this assembly. Thus, perfect chemical control can be maintained also in the cross-linking process, although this is not always necessary and more random cross-linking methods can be used. Incorporating photoactivatable groups, like azido adenosine or bromo- or iodo uridine, into oligonucleotide chains allows photochemical cross-linking, which is site specific. Also use the 3-thioribose in oligonucleotide and cysteine in the peptide spacer allows formation of disulphide bridges.

7. Preparation of Components for Liposomes

Many naturally occurring proteins may be used as such without any modification. Because in some cases these liposomes are used in vivo in humans, the human proteins should be used to minimize unwanted host immune responses. Human proteins can be produced in transgenic plants or animals. The amino acid sequence of proteins may also be altered through well-known genetic engineering techniques to produce mutated proteins having the desired biological functions of corresponding naturally occurring protein, but adapted to coupling to lipid molecules. For example, addition of a cysteine residue, either through substitution or inserting, will add a free thiol group for coupling to a lipid molecule. Moreover the location of this cysteine can be deliberately chosen. It should be located so that conjugation does not disturb the activity of the protein. Normally this means that the cysteine must be as far as possible from the active site.

In order to covalently couple a lipid with an effector molecule, the lipid must contain a functional group which has high enough reactivity with heterobifunctional cross-linker. Phosphatidylethanol-amines (PE) have free aliphatic amino group and can be used directly for conjugation. The conjugation of phosphatidylethanolamines (PE) and serines (PS) with proteins is well known in the literature (Egger et. al. Biochem. Biophys. Acta 1104 (1992) 45–54). Especially, if the protein contains a thiol group, a chemically well defined conjugate may be easily prepared. Several spacers are commercially available to couple two molecules, which contain an amino and a thiol group. If a protein does not contain an a thiol group, an aliphatic amino group, may be used for conjugation. Thiol groups are preferred for conjugation sites in proteins as compared with amino groups because of the lower abundance of thiol groups in most proteins.

Proteins can also be conjugated with lipids after the preparation of the liposomes so as to position the proteins on the outer surface of the liposome.

Phospholipids having unnatural stereochemistry may be prepared as described in the literature, for example see, (J. A. Virtanen et. al., Chem. Phys. Lipids 27 (1980) 185). Mannitol is tritylated to yield 1,6-ditrityl-D-mannitol, which is oxidized with lead tetra-acetate and the product reduced with sodium borohydride to yield 1-trityl-sn-glycerol (1-TrG). Diacylglycerols and phospholipids can be prepared starting from 1-TrG by standard methods. For the liposomes described in this application ether bond is preferred at least in the primary hydroxyl group, because it is resistant against lipase. in sn-hydroxyl ester bond can be used, because unnatural stereochemistry will make this bond stable against phospholipase A2. Instead of glycerophospholipids sphingolipids or completely artificial lipids, which are resistant against these enzymes, can be used.

8. Examples of Effector Molecule Combinations for Specific Diseases

Binding molecule-multienzyme complexes may be designed so as to treat diseases caused by specific pathogenic agents. Examples of effector molecule combinations are provided below in table 3 so that from each of the three columns (titled:antibodies, enzymes and peptides) suitable effector molecules are chosen. Binding molecule-multienzyme complexes, as described in this example, may contain one or several antibodies, which can be different or the same as one another. The binding molecule-multienzyme complexes may comprise 3–8 different enzymes as therapeutic effector molecules, which are typically selected so that 1–3 of the enzymes degrade lipids, 0–3 of the enzymes degrade proteins, 1–2 of the enzymes degrade nucleic acids and 0–3 of the enzymes degrade carbohydrates. Chemotactic peptides may be used as effector molecules enhance the natural defence mechanisms of the organism for treatment. Platelet aggregation inhibitors may also be used as effector molecules to prevent bacterial adhesion to human cells. Additionally, components such as coenzymes, cholic acids, polyamines and metal chelates can be included. These additional compounds may be used to activate enzymes or facilitate accessibility to the binding target so that enzymatic therapeutic effector molecules may more readily degrade the target. The binding molecule-multienzyme complexes may be also loaded into another assembly so that enzymes are activated at the target site. For example, instead of active enzymes, proenzymes may be used. When proenzymes are employed as therapeutic effector molecules. In this case a small amount of activating enzyme is brought into the target.

TABLE 3

| Antibodies: | Enzymes: | Peptides: |
|---|---|---|
| | VIRUSES | |
| Anti gp41 (HIV) | Phospholipase A₂ | Chemotactic |
| Anti gp120 (HIV) | Phospholipase C | peptides, e.g., |
| | Lipase | N-Formyl-Met |
| Anti hepatitis B | Cholesterol esterase | Leu—Phe |
| | Cholesterol oxidase | |
| | Aminopeptidase | |
| | Endoproteinase Arg—C | |
| | Endoproteinase Asp—N | |
| | Endoproteinase Lys—C | |
| | Carboxypeptidase A | |
| | Carboxypeptidase B | |
| | Chymotrypsin | |
| | Ribonuclease A | |
| | Ribonuclease B | |
| | Ribonuclease C | |
| | BACTERIA, PROTOZOA AND FUNGI | |
| Anti TB | α-Amylase | Chemotactic |
| (Mycobacterium | β-Amylase | peptides, e.g., |
| tuberculosis) | Galactosidase | N-Formyl-Met— |
| | Galactose oxidase | Leu—Phe |
| Anti Syphilis | α-Mannosidase | |
| (Treponema | β-Mannosidase | Platelet aggre- |
| pallidum) | | gation inhibitors, |
| | Phospholipase A₂ | e.g., Arg—Gly—Asp— |
| Anti Cholera | Phospholipase C | Ser |
| (Vibrio | Lipase | |
| Cholerae) | Cholesterol esterase | |
| | Lysozyme | |
| | Lactoferrin | |
| Anti plasmodium | Aminopeptidase | |
| | Endoproteinase Arg—C | |
| | Endoproteinase Asp—N | |
| | Endoproteinase Lys—C | |
| | Carboxypeptidase A | |
| | Carboxypeptidase B | |
| | Chymotrypsin | |
| | CANCER | |
| HUMAbSK1 | α-Amylase | Chemotactic |
| | β-Amylase | peptides, e.g., |
| Humanized | Galactosidase | N-Formyl-Met— |
| antimucin | Galactose oxidase | Leu—Phe |

TABLE 3-continued

| Antibodies: | Enzymes: | Peptides: |
|---|---|---|
| | α-Mannosidase | |
| | β-Mannosidase | Platelet aggre- |
| | | gation inhibitors, |
| | Phospholipase A₂ | e.g., Arg—Gly—Asp— |
| | Phospholipase C | Ser |
| | Lipase | |
| | Cholesterol esterase | |
| | Aminopeptidase | |
| | Endoproteinase Arg—C | |
| | Endoproteinase Asp—N | |
| | Endoproteinase Lys—C | |
| | Carboxypeptidase A | |
| | Carboxypeptidase B | |
| | Chymotrypsin | |
| | Alkaline phosphatase | |
| | Polyphenol oxidase | |
| | ATHEROSCLEROSIS | |
| Murine/Human | Phospholipase A₂ | Chemotactic |
| IgG1Z2D3 | Phospholipase C | peptides, e.g., |
| | Lipase | N-Formyl-Met— |
| | Cholesterol esterase | Leu—Phe |
| | Cholesterol oxidase | |
| | Aminopeptidase | Platelet aggre- |
| | Endoproteinase Arg—C | gation inhibitors, |
| | Endoproteinase Asp—N | e.g., Arg—Gly—Asp— |
| | Endoproteinase Lys—C | Ser |
| | Carboxypeptidase A | |
| | Carboxypeptidase B | |
| | Chymotrypsin | |
| | Collagenase | |

Incorporation by Reference

All patents, patents applications, and publications cited are incorporated herein by reference.

5. Equivalents

The foregoing written specification is considered to be sufficient to enable one skilled in the art to practice the invention. Indeed, various modifications of the above-described makes for carrying out the invention which are obvious to those skilled in the field of molecular biology, organic chemistry, or related fields are intended to be within the scope of the following claims.

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 21 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: misc_feature
        ( B ) LOCATION: 20..21
        ( D ) OTHER INFORMATION: /note= "Where N = X =

MMT-AP- CEDIPPA = N-Monomethoxytrityl aminopropyl
cyanoethyl N,N-diisopropylphosphoramidite"

( x i ) SEQUENCE DESCRIPTION: SEQ ID NO:1:

TGGAGATGGG GCACCATGCT N                                                    21

( 2 ) INFORMATION FOR SEQ ID NO:2:

( i ) SEQUENCE CHARACTERISTICS:
        ( A ) LENGTH: 50 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: misc_feature
        ( B ) LOCATION: 21..22
        ( D ) OTHER INFORMATION: /note= "Where Y = FMOC-DMT-SER-CEDIPPA
            = N-Fluorenylmethoxycarbonyl o-dimethoxytriphenyl serinyl
            cyanoethyl N,N-diisopropylphosphoramidite"

( x i ) SEQUENCE DESCRIPTION: SEQ ID NO:2:

AGCATGGTGC CCCATCTCCA YAGTCACAGC ACAGCACTAA TAACAAGAAA                      50

( 2 ) INFORMATION FOR SEQ ID NO:3:

( i ) SEQUENCE CHARACTERISTICS:
        ( A ) LENGTH: 31 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: misc_feature
        ( B ) LOCATION: 2..3
        ( D ) OTHER INFORMATION: /note= "Where Y = FMOC-DMT-SER-CEDIPPA
            = N-Fluorenylmethoxycarbonyl O-dimethoxytriiphenyl srinyl
            cyanoethyl N,N-diisopropylphosphoramidite"

( x i ) SEQUENCE DESCRIPTION: SEQ ID NO:3:

T YTTTCTTGT TATTAGTGCT GTGCTGTGAC T                                         31

( 2 ) INFORMATION FOR SEQ ID NO:4:

( i ) SEQUENCE CHARACTERISTICS:
        ( A ) LENGTH: 25 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: misc_feature
        ( B ) LOCATION: 24..25
        ( D ) OTHER INFORMATION: /note= "Where N = X =
            MMT-AP- CEDIPPA = N-Monomethoxytrityl aminopropyl
            cyanoethyl N,N-diisopropylphosphoramidite"

( x i ) SEQUENCE DESCRIPTION: SEQ ID NO:4:

GTGATAGGAG TTGATTACAG TCCTN                                                 25

( 2 ) INFORMATION FOR SEQ ID NO:5:

( i ) SEQUENCE CHARACTERISTICS:
        ( A ) LENGTH: 49 base pairs
        ( B ) TYPE: nucleic acid
        ( C ) STRANDEDNESS: unknown ( D ) TOPOLOGY: unknown ( i i ) MOLECULE TYPE: DNA (genomic)

( i x ) FEATURE:
    ( A ) NAME/KEY: misc_feature
    ( B ) LOCATION: 25..26
    ( D ) OTHER INFORMATION: /note= "Where Y = FMOC-DMT-SER-CEDIPPA
        = N-Flourenylmethoxycarbonyl O-dimethyoxytripheynyl
        serinyl cyanoethy N,N-diisopropylphosphoramidite"

( x i ) SEQUENCE DESCRIPTION: SEQ ID NO:5:

AGGACTGTAA TCAACTCCTA TCAC Y ATCAG AAGAGTGAGA CGGTGGGAT    49

( 2 ) INFORMATION FOR SEQ ID NO:6:

( i ) SEQUENCE CHARACTERISTICS:
        ( A ) LENGTH: 26 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: misc_feature
        ( B ) LOCATION: 2..3
        ( D ) OTHER INFORMATION: /note= "Where Y =
        FMOC-DMT-SER- CEDIPPA = N-Monomethoxytrityl aminopropyl
        cyanoethyl N,N-diisopropylphosphoramidite "

( x i ) SEQUENCE DESCRIPTION: SEQ ID NO:6:

T Y ATCCCACC GTCTCACTCT TCTGAT    26

( 2 ) INFORMATION FOR SEQ ID NO:7:

( i ) SEQUENCE CHARACTERISTICS:
        ( A ) LENGTH: 25 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: misc_feature
        ( B ) LOCATION: 24..25
        ( D ) OTHER INFORMATION: /note= "Where X = N =
        MMMT-AP- CEDIPPA = N-Monomethoxytrityl aminopropyl
        cyanoethyl N,N-diisopropylphosphoramidite"

( x i ) SEQUENCE DESCRIPTION: SEQ ID NO:7:

TAGACTCAGC GCAATCGTGA AGCTN    25

( 2 ) INFORMATION FOR SEQ ID NO:8:

( i ) SEQUENCE CHARACTERISTICS:
        ( A ) LENGTH: 49 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: misc_feature
        ( B ) LOCATION: 25..26
        ( D ) OTHER INFORMATION: /note= "Where Y =
        FMOC-DMT-SER- CEDIPPA = N-Fluroenylmethoxycarbonyl
        O- dimethoxytriphenyl serinyl cyanoethyl
        N,N- diisopropylphosphoramidite"

( x i ) SEQUENCE DESCRIPTION: SEQ ID NO:8:

```
AGCTTCACGA  TTGCGCTGAG  TCTA Y GATTC  TCGGCTCGTT  CGAAGTGTC                    4 9
```

( 2 ) INFORMATION FOR SEQ ID NO:9:

( i ) SEQUENCE CHARACTERISTICS:
        ( A ) LENGTH: 26 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: misc_feature
        ( B ) LOCATION: 2..3
        ( D ) OTHER INFORMATION: /note= "Where Y =
        FMOC-DMT-SER- CEDIPPA = N-Fluorenylmethoxycarbonyl
        O- dimethoxytriphenyl serinyl cyanoethyl
        N,N- diisopropylphophoramidite"

( x i ) SEQUENCE DESCRIPTION: SEQ ID NO:9:

```
T Y GACACTTC  GAACGAGCCG  AGAATC                                                2 6
```

What is claimed is:

1. A targetable antiviral liposomal composition comprising:
  a liposome,
  a target-binding moiety, said moiety being a polypeptide, glycoprotein, or glycoprotein fragment having viral specificity, and
  a therapeutic hydrolytic enzyme capable of digesting a viral component to reduce virus activity,
  wherein at least one molecule of said target-binding moiety and at least one molecule of said hydrolytic enzyme are functionally coupled to the outer surface of said liposome.

2. The antiviral liposomal composition of claim 1, wherein said target-binding moiety is specific for a viral protein.

3. The antiviral liposomal composition of claim 1, wherein said therapeutic enzyme is selected from the group consisting of glycosidases, phospholipases, lipases, cholesterol esterases, nucleases, and proteases.

4. The antiviral liposomal composition of claim 1, wherein said therapeutic enzyme is a glycosidase.

5. The antiviral liposomal composition of claim 1, wherein said therapeutic enzyme is a phospholipase.

6. The antiviral liposomal composition of claim 5, wherein said phospholipase is phospholipase $A_2$.

7. The antiviral liposomal composition of claim 5, wherein said phospholipase is phospholipase C.

8. The antiviral liposomal composition of claim 1, wherein said therapeutic enzyme is a lipase.

9. The antiviral liposomal composition of claim 1, wherein said therapeutic enzyme is a cholesterol esterase.

10. The antiviral liposomal composition of claim 1, wherein said therapeutic enzyme is a nuclease.

11. The antiviral liposomal composition of claim 10, wherein said nuclease is a ribonuclease.

12. The antiviral liposomal composition of claim 11, wherein said ribonuclease is selected from the group consisting of ribonuclease A, ribonuclease B, and ribonuclease C.

13. The antiviral liposomal composition of claim 11, wherein said ribonuclease is ribonuclease A.

14. The antiviral liposomal composition of claim 11, wherein said ribonuclease is ribonuclease B.

15. The antiviral liposomal composition of claim 12, wherein said ribonuclease is ribonuclease C.

16. The antiviral liposomal composition of claim 1, wherein said therapeutic enzyme is a protease.

17. The antiviral liposomal composition of claim 1, further comprising a second therapeutic enzyme.

18. The antiviral liposomal composition of claim 1, further comprising a second target-binding moiety having viral specificity.

19. The antiviral liposomal composition of claim 1, wherein said target-binding moiety is specific for an enveloped virus.

20. The antiviral liposomal composition of any one of claims 3, wherein said target-binding moiety is specific for HIV-1.

21. The antiviral liposomal composition of claim 20, wherein said target-binding moiety is specific for HIV-1 gp120.

22. The antiviral liposomal composition of claim 20, wherein said target-binding moiety is specific for HIV-1 gp41/160.

23. The antiviral liposomal composition of claim 20, wherein said target-binding moiety includes soluble CD4.

24. The antiviral liposomal composition of claim 20, further comprising an antisense oligonucleotide hybridizable to the HIV genome.

25. The antiviral liposomal composition of claim 1, wherein said target-binding moiety is specific for influenza virus.

26. The antiviral liposomal composition of claim 1, wherein said target-binding moiety is specific for a hepatitis virus.

27. The antiviral liposomal composition of claim 1, further comprising albumin coupled to the surface of said liposome.

28. The antiviral liposomal composition of claim 1, further comprising, internal to said liposome, a hydrolytic enzyme capable of digesting a viral component to reduce virus activity.

* * * * *